US011118167B2

(12) United States Patent
Stone et al.

(10) Patent No.: US 11,118,167 B2
(45) Date of Patent: Sep. 14, 2021

(54) ENZYME-MEDIATED DEPLETION OF ADENOSINE AND/OR METHYLTHIOADENOSINE

(71) Applicant: BOARD OF REGENTS, THE UNIVERSITY OF TEXAS SYSTEM, Austin, TX (US)

(72) Inventors: Everett Stone, Austin, TX (US); Donjeta Gjuka, Austin, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 16/950,622

(22) Filed: Nov. 17, 2020

(65) Prior Publication Data
US 2021/0095264 A1 Apr. 1, 2021

Related U.S. Application Data

(63) Continuation of application No. 16/956,340, filed as application No. PCT/US2018/066731 on Dec. 20, 2018.

(60) Provisional application No. 62/609,000, filed on Dec. 21, 2017.

(51) Int. Cl.
| | |
|---|---|
| A61K 47/60 | (2017.01) |
| C12N 9/10 | (2006.01) |
| A61K 47/68 | (2017.01) |
| A61P 35/02 | (2006.01) |
| A61P 35/04 | (2006.01) |
| A61K 38/45 | (2006.01) |
| A61K 39/395 | (2006.01) |
| C07K 16/28 | (2006.01) |
| C12N 9/96 | (2006.01) |
| C12Q 1/6886 | (2018.01) |
| G01N 33/573 | (2006.01) |
| G01N 33/574 | (2006.01) |
| A61K 39/00 | (2006.01) |

(52) U.S. Cl.
CPC .......... C12N 9/1077 (2013.01); A61K 38/45 (2013.01); A61K 39/3955 (2013.01); A61K 47/60 (2017.08); A61K 47/6849 (2017.08); A61K 47/6851 (2017.08); A61K 47/6855 (2017.08); A61P 35/02 (2018.01); A61P 35/04 (2018.01); C07K 16/2818 (2013.01); C12N 9/96 (2013.01); C12Q 1/6886 (2013.01); C12Y 204/02028 (2013.01); G01N 33/573 (2013.01); G01N 33/574 (2013.01); A61K 2039/505 (2013.01); C07K 2317/622 (2013.01); C07K 2317/76 (2013.01); C07K 2319/30 (2013.01); C07K 2319/33 (2013.01); C12Q 2600/106 (2013.01); C12Q 2600/156 (2013.01)

(58) Field of Classification Search
CPC .................................................... C12N 9/1077
USPC ........................................................ 424/134.1
See application file for complete search history.

(56) References Cited

U.S. PATENT DOCUMENTS

| | | | |
|---|---|---|---|
| 6,870,037 B1 | 3/2005 | Olopade | |
| 2004/0247600 A1* | 12/2004 | Leoni ............... | G01N 33/57496 424/146.1 |
| 2011/0053236 A1 | 3/2011 | Walmsley et al. | |

FOREIGN PATENT DOCUMENTS

| | | |
|---|---|---|
| WO | WO 01/83780 | 11/2011 |
| WO | WO 2012/131052 | 10/2012 |

OTHER PUBLICATIONS

Bertino et al., Targeting tumors that lack methylthioadenosine phosphorylase (MTAP) activity: current strategies. *Cancer Biology & Therapy*, 11(7): 627-632, 2011.
Bradford et al.. Adenosine deaminase (ADA)-deficient severe combined immune deficiency (SCID): molecular pathogenesis and clinical manifestations. *Journal of Clinical Immunology*, 37(7): 626-637, 2017.
Camacho-Vanegas et al., Primate genome gain and loss: a bone dysplasia, muscular dystrophy, and bone cancer syndrome resulting from mutated retroviral-derived MTAP transcripts. *The American Journal of Human Genetics*, 90(4): 614-627, 2012.
Castle et al., Immunomic, genomic and transcriptomic characterization of CT26 colorectal carcinoma. *BMC Genomics*, 15:190, 2014.
Dozier, Jonathan K., and Mark D. Distefano. "Site-specific PEGylation of therapeutic proteins." *International journal of molecular sciences* 16.10 (2015): 25831-25864.
English Translation of WO 01/83780, provided by the International Search Authority dated Sep. 5, 2019.
Gao, Jianjun, et al. "Loss of IFN-γ pathway genes in tumor cells as a mechanism of resistance to anti-CTLA-4 therapy." *Cell* 167.2 (2016): 397-404,.
Henrich et al., Suppressive effects of tumor cell-derived 5'-deoxy-5'-methylthioadenosine on human T cells. *OncoImmunology*, 5(8): e1184802, 2016.
Hoover et al., The structure of human macrophage inflammatory protein-3alpha /CCL20. Linking antimicrobial and CC chemokine receptor-6-binding activities with human beta-defensins. *J Biol Chem*, 277(40):37647-37654, 2002.

(Continued)

Primary Examiner — Sean E Aeder
(74) Attorney, Agent, or Firm — Parker Highlander PLLC

(57) ABSTRACT

Methods and compositions related to the engineering of a protein with MTA/ADO-degrading enzyme activity are described. For example, in certain aspects there may be disclosed an MTase capable of degrading MTA/ADO. Furthermore, certain aspects of the invention provide compositions and methods for the treatment of cancer or SCID with an MTase using the disclosed proteins or nucleic acids.

15 Claims, 8 Drawing Sheets
Specification includes a Sequence Listing.

(56) References Cited

OTHER PUBLICATIONS

International Preliminary Report on Patentability issued in International Application No. PCT/US18/66731, dated Jul. 2, 2020.
International Search Report and Written Opinion issued in International Application No. PCT/US18/66731, dated May 9, 2019.
Invitation to Pay Additional Fees issued in International Application No. PCT/US 18/66731, dated Mar. 12, 2019.
Jiang et al., Comprehensive evaluation of NT5E/CD73 expression and its prognostic significance in distinct types of cancers. *BMC Cancer*, 18:267, 2018.
Kadariya et al., Mice heterozygous for germ-line mutations in methylthioadenosine phosphorylase (MTAP) die prematurely of T-cell lymphoma. *Cancer Research*, 69(14): 5961-5969,2009.
Keyel et al., Metbyltbioadenosine reprograms macrophage activation through adenosine receptor stimulation. *PLoS One*, 9(8): e104210, 2014.
Kim et al., Downregulation of methylthioadenosine phosphorylase by homozygous deletion in gastric carcinoma. *Genes, Chromosomes and Cancer*, 50(6): 421-433, 2011.
Kirovski et al., Down-regulation of methylthioadenosine phosphorylase (MTAP) induces progression of hepatocellular carcinoma via accumulation of 5'-deoxy-5'-methylthioadenosine (MTA). *American Journal of Pathology*, 178(3): 1145-1152, 2011.
Lewandowski, Angela T., et al. "Towards area-based in vitro metabolic engineering: Assembly of Pfs enzyme onto patterned microfabricated chips." *Biotechnology progress* 24.5 (2008): 1042-1051.
Morello et al., Soluble CD73 as biomarker in patients with metastatic melanoma patients treated with nivolumab. *Journal of Translational Medicine*, 15:244, 2017.
Rau, Doris, Karl Kramer, and Bertold Hock. "Single-chain Fv antibody-alkaline phosphatase fusion proteins produced by one-step cloning as rapid detection tools for ELISA." *Journal of Immunoassay and Immunochemistry* 23.2 (2002): 129-143.
Sek et al., Targeting Adenosine Receptor Signaling in Cancer Immunotherapy. *International J. of Mol. Sciences*, 19:3837, 2018.
Singh et al., Picomolar transition state analogue inhibitors of human 5'-methylthioadenosine phosphorylase and X-ray structure with MT-Immucillin-A. *Biochemistry*, 43(1): 9-18, 2004.
Stevens et al., Direct and tumor microenvironment mediated influences of 5'-deoxy-5'-(methylthio) adenosine on tumor progression of malignant melanoma. *Journal of Cellular Biochemistry*, 106(2): 210-219, 2009.
Stevens et al., Quantification of intermediates of the methionine and polyamine metabolism by liquid chromatography—tandem mass spectrometry in cultured tumor cells and liver biopsies. *Journal of Chromatography*, A 1217(19): 3282-3288, 2010.
Stevens et al., Quantitative analysis of 5'-deoxy-5'-methylthioadenosine in melanoma cells by liquid chromatography-stable isotope ratio tandem mass spectrometry. *Journal of Chromatography B*, 876(1): 123-128, 2008.
Stone et al., Strategies for optimizing the serum persistence of engineered human arginase I for cancer therapy. *Journal of Controlled Release*, 158:171-179, 2012.
Sun et al., Fasting inhibits colorectal cancer growth by reducing M2 polarization of tumor-associated macrophages. *Oncotarget*, 8:74649-74660, 2017.
Tiziani et al., Metabolomics of the tumor microenvironment in pediatric acute lymphoblastic leukemia. *PLoS One*, 8:e82859, 2013.
Tiziani et al., Optimized metabolite extraction from blood serum for 1H nuclear magnetic resonance spectroscopy. *Analytical Biochemistry*, 377:16-23, 2008.
Vandenbark et al., Inhibition of lymphocyte transformation by a naturally occurring metabolite: 5'-Methylthioadenosine. *Cellular Immunology*, 49(1): 26-33, 1980.
Vijayan et al., Targeting immunosuppressive adenosine in cancer. *Nature Reviews Cancer*, 17:709, 2017.
Ward, Proc, Embo-Alko Workshop on Molecular Biology of Filamentous Fungi, Helsinki, 119-128, 1989.
Woollard et al., Independent Loss of Methylthioadenosine Phosphorylase (MTAP) in Primary Cutaneous T-Cell Lymphoma. *Journal of Investigative Dermatology*. 136(6): 1238-1246, 2016.
Yu et al., Ecto-5'-nucleotidase expression is associated with the progression of renal cell carcinoma. Oncology Letters, 9:2485-2494, 2015.

\* cited by examiner

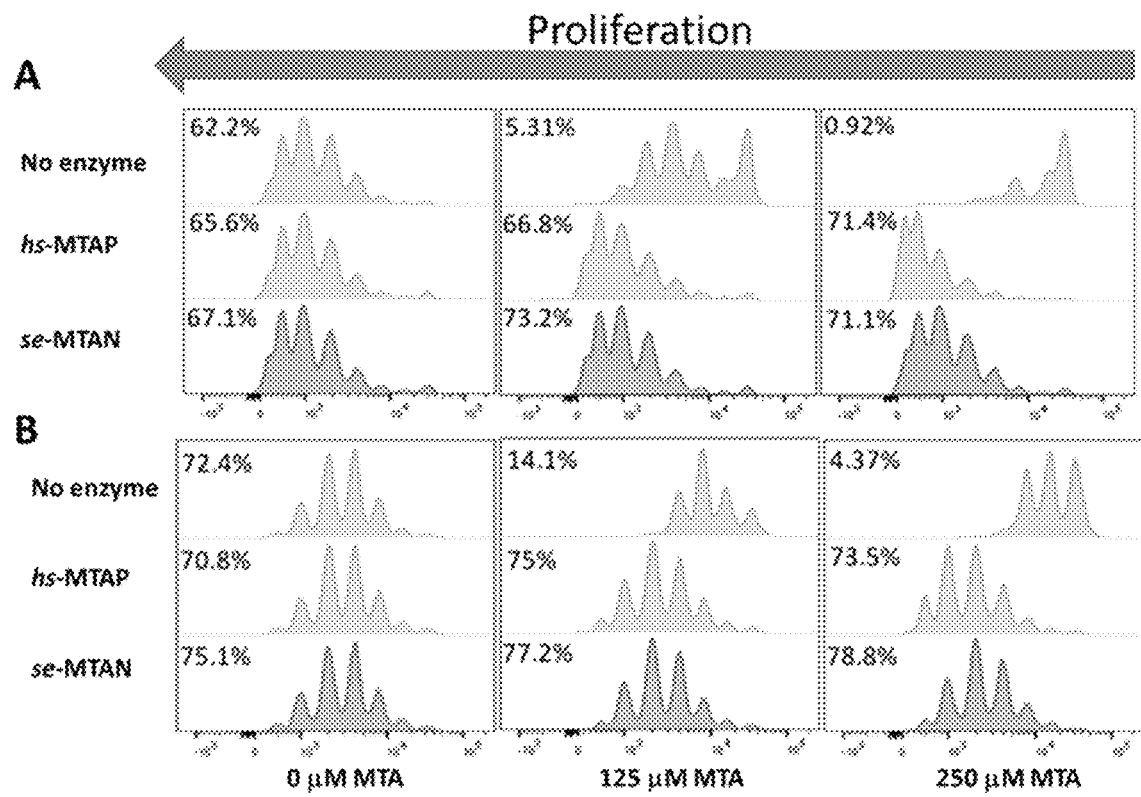
FIGS. 5A-B
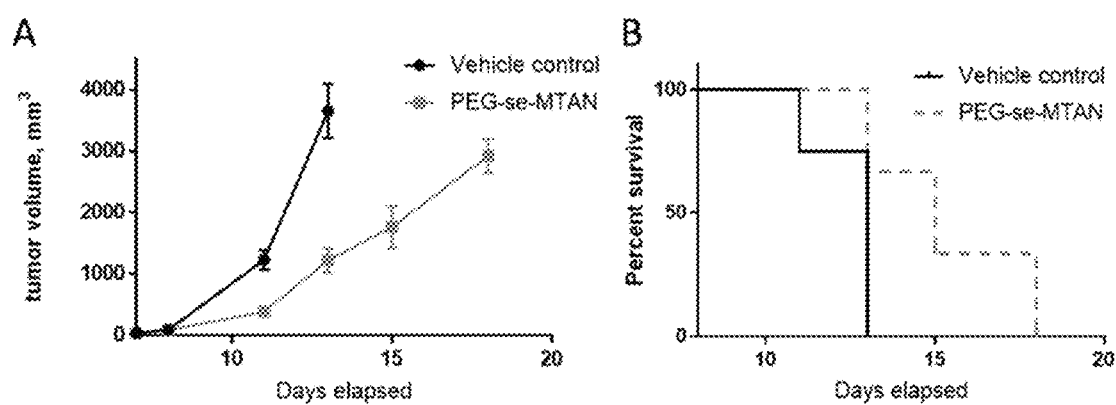
FIGS. 6A-B

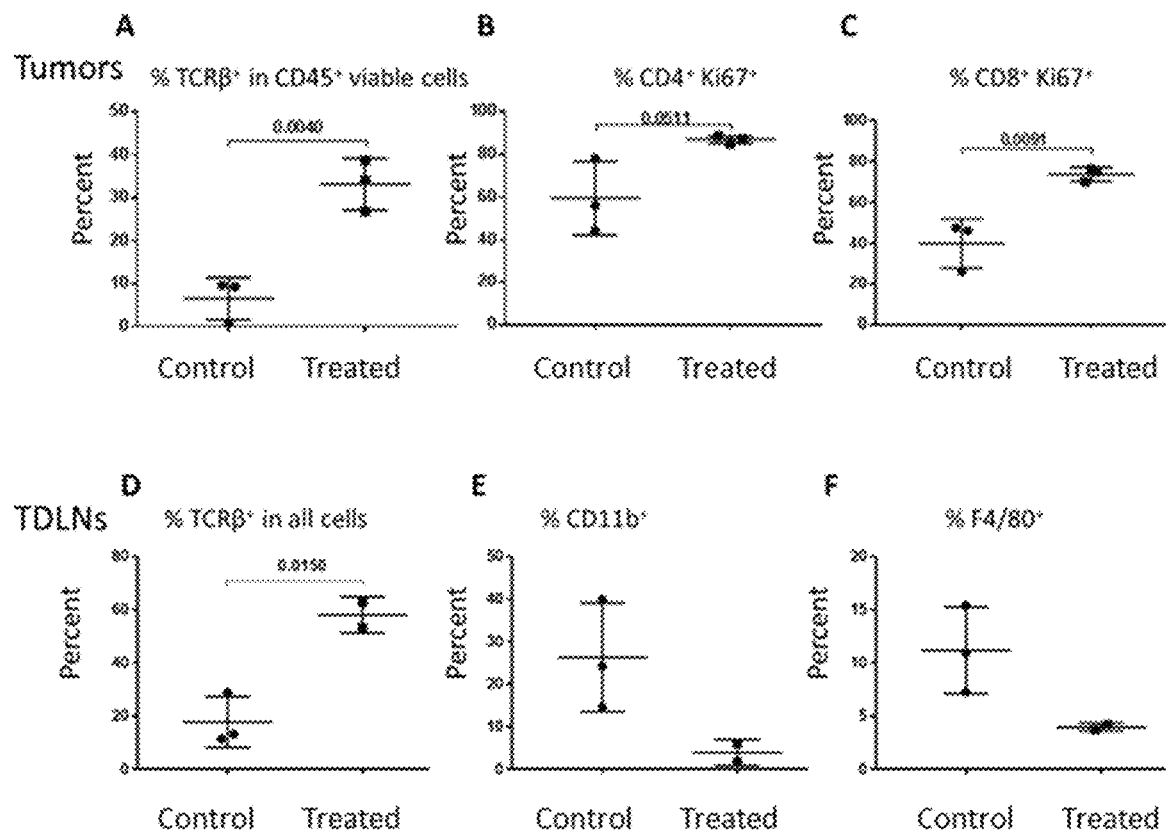
FIGS. 7A-F
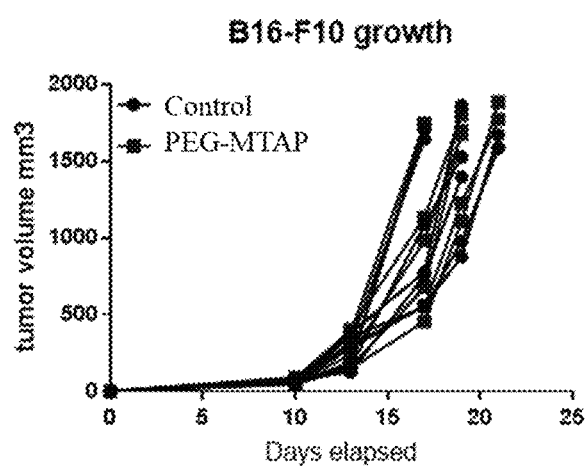
FIG. 8A

ENZYME-MEDIATED DEPLETION OF ADENOSINE AND/OR METHYLTHIOADENOSINE

REFERENCE TO RELATED APPLICATIONS

The present application is continuation of United Stated application Ser. No. 16/956,340, filed Jun. 19, 2020, as a national phase application under 35 U.S.C. § 371 of International Application No. PCT/US2018/066731, filed Dec. 20, 2018, which claims the priority benefit of U.S. provisional application No. 62/609,000, filed Dec. 21, 2017, the entire contents of each of which is incorporated herein by reference.

STATEMENT REGARDING FEDERALLY SPONSORED RESEARCH

This invention was made with government support under Grant No. R01 CA189623 awarded by the National Institutes of Health. The government has certain rights in the invention.

BACKGROUND

1. Field

The present invention relates generally to the fields of medicine and biology. More particularly, it concerns compositions for the treatment of cancer or SCID with enzymes that deplete adenosine and/or methylthioadenosine (MTA). Even more particularly, it concerns the engineering, pharmacological optimization, and use of prokaryotic and human enzymes with adenosine- and/or MTA-degrading activity suitable for human therapy.

2. Description of Related Art

Homozygous genetic deletion at chromosome 9p21 of methylthioadenosine phosphorylase (MTAP) is a common event observed in ~30-40% of osteosarcomas, pancreatic cancers, and chordomas, with even higher losses (60-75%) noted in mesothelioma, T-cell acute lymphoblastic leukemias, and gliomas (Bertino et al., 2011). MTAP degrades methylthioadenosine (MTA), a byproduct of polyamine synthesis, into methylthioribose-1'-phosphate (MTR-1'-P) and adenine, which are recycled into the methionine and purine salvage pathways. MTAP loss is correlated with aggressive disease and worse outcomes. MTAP deletion in solid tumors and lymphomas results in an accumulation and increased secretion of its substrate—MTA (Stevens et al., 2008; Stevens et al., 2009; Stevens et al., 2010). A study in melanoma cells reported that significantly higher MTA concentrations in tumors versus in normal tissue correlated with more pronounced characteristics of invasiveness and malignancy (Stevens et al., 2009). Similarly, MTAP deficiency in hepatocellular carcinoma (HCC) also showed a strong correlation with increased MTA levels and HCC proliferation and increased the pro-tumorigenic gene expression profile in hepatic stellate cells (Kirovski et al., 2011).

Loss of the MTAP gene was commonly thought to be a simple bystander co-deletion along with CDKN2, a cell cycle regulator, due to their proximity on chromosome 9p21. However, in studies of gastric carcinoma and cutaneous T-cell lymphomas, MTAP deletions were found to occur independently of CDKN2 loss and correlate with worse outcomes (Kim et al., 2011; Woollard et al., 2016). In a murine knockout model, it was found that while homozygous MTAP$^{-/-}$ null mice have an embryonically lethal phenotype, MTAP$^{+/-}$ heterozygotes develop normally but die prematurely of T-cell lymphoma (Kadariya et al., 2009). In line with these findings, the autosomal dominant hereditary malignancy, diaphyseal medullary stenosis with malignant fibrous histiocytoma (DMSMFH), results from mutations within the MTAP gene that lead to exon skipping, alternative splicing, and ultimately a dysfunctional MTAP gene product, indicative of a tumor suppressive role independent of CDKN2 (Camacho-Vanegas et al., 2012).

Deletion or repression of MTAP leads to the buildup and excretion of MTA, which was recently shown to have potent immunosuppressive properties. Incubation with MTA halts the proliferation and differentiation of naïve lymphocytes and is cytotoxic to activated human T cells. In particular, MTA halts the expansion of antigen-specific CD8$^+$ T cells, prevents the upregulation of activation markers, such as CD25 and CD69, and induces apoptosis in pre-stimulated cytotoxic T lymphocytes (Henrich et al., 2016). Earlier reports have also indicated that exogenous MTA inhibits DNA synthesis, protein synthesis, and proliferation of human lymphocyte cultures stimulated with antigens or allogeneic cells, an effect that could be reversed by washing the cells free of MTA (Vandenbark et al., 1980). While the mechanism of how MTA exerts its effects is not fully worked out, there is evidence that MTA can act as an agonist of the adenosine receptors A2a and A2b, creating a tolerogenic phenotype in macrophages (Keyel et al., 2014). Similarly, in experiments with malignant melanoma, MTA was observed to cause a tumor promoting role in fibroblasts by induction of basic fibroblast growth factor (bFGF) and matrix metalloproteinase 3 (MMP3) (Stevens et al., 2009). The evidence that the consequence of MTAP deletion acts to suppress immune effector cells and promote tolerogenic stromal cell phenotypes through the buildup of MTA now suggests a clear mechanism for why this is one of the most common gene deletions in cancer. Tumor excreted MTA may be considered an immune checkpoint that helps tumor cells evade immune surveillance and elimination.

In addition, the adenosinergic pathway has emerged as a major therapeutic target for cancer therapy due to its role in tumor microenvironment (TME) immunosuppression. Extracellular adenosine (ADO) arises from the action of ectonucleotidases CD39 and CD73 and/or by release from dying cells wherein it acts as an immunosuppressive signaling molecule by binding adenosine receptors. CD39 converts ATP and ADP into AMP and CD73 converts AMP into ADO which in turn can bind to one of the four known G-protein coupled ADO receptors (AIR, A2AR, A2BR, and A3R) (Sek et al., 2018). Accumulating evidence indicates that one of the mechanisms of innate and acquired resistance to antibody immune checkpoint inhibitors, such as anti-PD/L1 or anti-CTLA4, is due to the accumulation of ADO in the tumor microenvironment (Vijayan et al., 2017). In a separate study of metastatic melanoma patients being treated with nivolumab, it was found that tumor expression of high levels of CD73 was significantly associated with poor overall survival and progression free survival (Morello et al., 2017). Similarly, it was found that renal cell carcinoma (RCC) patients with high CD73 expression displayed a 3.5 year shorter median survival as compared to low CD73 expressing patients (Yu et al., 2015). Furthermore, high CD73 expression has been shown to significantly correlate with lymph node metastases in gastric carcinoma, gallbladder cancer, and head and neck squamous cell carcinomas (Jiang et al., 2018) overall highlighting the role tumor derived ADO plays in immune escape and disease progression. As such, compositions and methods for reducing MTA and/or ADO levels in the tumor microenvironment are needed.

SUMMARY

Aspects of the present invention overcome a major deficiency in the art by providing novel enzymes that comprise bacterial and mammalian polypeptide sequences capable of degrading ADO and/or MTA, which may be suitable for cancer therapy and having improved pharmacological properties. In some aspects, the therapeutic may be derived from mammalian enzymes, such as the *Homo sapiens* methylthioadenosine phosphorylase (hs-MTAP), or alternatively from prokaryotic enzymes, such as the *Salmonella enterica* enzyme, methylthioadenosine nucleosidase (se-MTAN). In other aspects, there may be a polypeptide comprising either a native or modified human or mammalian MTAP capable of degrading ADO and/or MTA. In yet other aspects, there may be a polypeptide comprising either a native or modified se-MTAN or prokaryotic MTAN capable of degrading ADO and/or MTA. In some aspects, the polypeptide may be capable of degrading ADO and/or MTA under physiological conditions.

Numerous mutations of adenosine deaminase (ADA) are known to occur and result in severe combined immune deficiency (SCID). ADA deficiency results in the buildup of intra and extra-cellular ADO leading to thymic apoptosis and a profound pan-lymphopenia. The buildup of ADO and other metabolites arising from ADA deficiency is considered the primary cause of lymphotoxicity. Patients with ADA deficiency often further display symptoms such as developmental delays, chronic diarrhea, skin rashes, pneumonia, and extensive dermatitis. Current treatments include allogeneic hematopoietic stem cell transplantation, enzyme replacement therapy using PEGylated bovine ADA (PEG-ADA), and gene therapy with autologous gene corrected hematopoietic stem cells (Bradford et al., 2017). Aspects of the present invention provide enzymes that comprise bacterial and mammalian polypeptide sequences capable of degrading ADO, which may be suitable for ADA SCID therapy by removing/degrading toxic levels of ADO.

The present invention concerns the engineering of mammalian MTAP or prokaryotic MTAN enzymes (i.e., MTase enzymes) such that ADO and/or MTA can be efficiently degraded from serum and tumor microenvironments, and providing the modified MTase enzymes in a formulation suitable for human cancer therapy and/or SCID therapy. ADO degrading enzymes and MTase enzymes modified as described herein provide novel enzymes that comprise human, primate, mammalian, or prokaryotic polypeptide sequences having ADO- and/or MTA-degrading catalytic activity as compared to the native enzyme. As such, these modified enzymes may be suitable for cancer therapy and/or SCID therapy and have low immunogenicity and improved serum stability.

Accordingly, in one embodiment there is provided a modified polypeptide, particularly an enzyme variant with ADO/MTA-degrading activity. For example, an enzyme variant may have an amino acid sequence selected from the group consisting of SEQ ID NOs: 1 or 3. For example, the variant may be derived from a human enzyme, such as human MTAP, or from a prokaryotic enzyme, such as *Salmonella enterica* MTAN. In certain aspects, there may be a polypeptide comprising a modified MTase capable of degrading ADO/MTA. In some embodiments, the polypeptide may be capable of degrading ADO/MTA under physiological conditions. For example, the polypeptide may have a catalytic efficiency for ADO/MTA ($k_{a}/K_{M}$) of at least or about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$ $s^{-1}M^{-1}$ or any range derivable therein.

An unmodified polypeptide may be a native MTAP and MTAN. For example, the native MTase may have the sequence of SEQ ID NO: 1 or 3. Exemplary native polypeptides include a sequence having about, at least 60%, 65%, 70%, 75%, 80%, 85%, 90%, 95%, 96%, 97%, 98%, 99% or 100% identity (or any range derivable therein) to SEQ ID NOs: 1 or 3 or a fragment thereof. For example, the native polypeptides may have a MTAP sequence according to any one of SEQ ID NOs: 5-40 or may have a MTAN sequence according to any one of SEQ ID Nos: 41-50. For example, the native polypeptide may comprise at least or up to about 10, 20, 30, 40, 50, 60, 70, 80, 90, 100, 150, 200, 250, or 300 residues (or any range derivable therein) of the sequence of SEQ ID NOs: 1 or 3.

In some embodiments, the native MTase may be modified by one or more other modifications, such as chemical modifications, substitutions, insertions, deletions, and/or truncations. In a particular embodiment, the native MTase may be modified by substitutions. For example, the number of substitutions may be one, two, three, four or more. In further embodiments, the native MTase may be modified in the substrate recognition site or any location that may affect substrate specificity or enhance catalytic activity.

In some aspects, the MTase enzyme is modified by being conjugated to an antibody. The antibody may be an scFv antibody. The antibody or scFv antibody may be an anti-MUC1 antibody, an anti-HER2 antibody, an anti-CTLA4 antibody, an anti-PD1 antibody, or an anti-PDL1 antibody.

A modified polypeptide as discussed above may be characterized as having a certain percentage of identity as compared to an unmodified polypeptide (e.g., a native polypeptide) or to any polypeptide sequence disclosed herein. For example, the unmodified polypeptide may comprise at least or up to about 10, 20, 30, 40, 50, 60, 70, 80, 90, 100, 150, 200, 250, or 300 residues (or any range derivable therein) of a native MTAP or MTAN. The percentage identity may be about, at least 60%, 65%, 70%, 75%, 80%, 85%, 90%, 95%, 96%, 97%, 98%, 99% or 100% (or any range derivable therein) between the unmodified portions of a modified polypeptide and the corresponding native polypeptide. It is also contemplated that percentage of identity discussed above may relate to a particular modified region of a polypeptide as compared to an unmodified region of a polypeptide. For instance, a polypeptide may contain a modified or mutant substrate recognition site of MTase that can be characterized based on the identity of the amino acid sequence of the modified or mutant substrate recognition site of MTase to that of an unmodified or mutant MTase from the same species or across species. For example, a modified or mutant human polypeptide characterized as having at least 90% identity to an unmodified MTase means that at least 90% of the amino acids in that modified or mutant human polypeptide are identical to the amino acids in the unmodified polypeptide.

In some aspects, the present invention also contemplates polypeptides comprising the modified MTase linked to a heterologous amino acid sequence. For example, the modified MTase may be linked to the heterologous amino acid sequence as a fusion protein. In a particular embodiment, the modified MTase may be linked to amino acid sequences, such as an IgG Fc, albumin, an albumin binding peptide, or an XTEN polypeptide for increasing the in vivo half-life.

To increase serum stability, the modified MTase may be linked to one or more polyether molecules. In a particular embodiment, the polyether may be polyethylene glycol (PEG). The modified polypeptide may be linked to PEG via specific amino acid residues, such as lysine or cysteine. For therapeutic administration, such a polypeptide comprising the modified MTase may be dispersed in a pharmaceutically acceptable carrier.

In some aspects, a nucleic acid encoding such a modified MTase is contemplated. In one aspect, the nucleic acid has been codon optimized for expression in bacteria. In particular embodiments, the bacteria is E. coli. In other aspects, the nucleic acid has been codon optimized for expression in a fungus (e.g., yeast), in insect cells, or in mammalian cells. The present invention further contemplates vectors, such as expression vectors, containing such nucleic acids. In particular embodiments, the nucleic acid encoding the modified MTase is operably linked to a promoter, including but not limited to heterologous promoters. In one embodiment, a modified MTase may be delivered to a target cell by a vector (e.g., a gene therapy vector). Such viruses may have been modified by recombinant DNA technology to enable the expression of the modified MTase-encoding nucleic acid in the target cell. These vectors may be derived from vectors of non-viral (e.g., plasmids) or viral (e.g., adenovirus, adeno-associated virus, retrovirus, lentivirus, herpes virus, or vaccinia virus) origin. Non-viral vectors are preferably complexed with agents to facilitate the entry of the DNA across the cellular membrane. Examples of such non-viral vector complexes include the formulation with polycationic agents which facilitate the condensation of the DNA and lipid-based delivery systems. An example of a lipid-based delivery system would include liposome-based delivery of nucleic acids.

In still further aspects, the present invention further contemplates host cells comprising such vectors. The host cells may be bacteria (e.g., E. coli), fungal cells (e.g., yeast), insect cells, or mammalian cells.

In some embodiments, the vectors are introduced into host cells for expressing the modified MTase. The proteins may be expressed in any suitable manner. In one embodiment, the proteins are expressed in a host cell such that the protein is glycosylated. In another embodiment, the proteins are expressed in a host cell such that the protein is aglycosylated.

In some embodiments, the polypeptides or nucleic acids are in a pharmaceutical formulation comprising a pharmaceutically acceptable carrier. The polypeptide may be a native MTase polypeptide or a modified MTase polypeptide. The nucleic acid may encode a native MTase polypeptide or a modified MTase polypeptide.

In one embodiment, methods are provided for treating a patient having or at risk of developing cancer comprising administering to the subject a therapeutically effective amount of a formulation comprising an isolated, modified MTase polypeptide that has MTase activity. In some aspects, the MTase polypeptide comprises a sequence having at least 90% identity to SEQ ID NO: 1 or 3. In some aspects, the MTase polypeptide has at least 95% identity to SEQ ID NO: 1 or 3. In some aspects, the MTase polypeptide has the sequence of SEQ ID NO: 1 or 3. In some aspects, the MTase is a prokaryotic MTAN, wherein the prokaryotic MTAN comprises an amino acid sequence at least 95% identical to SEQ ID NO: 3. In some aspects, the MTase is a human MTAP, wherein the human MTAP comprises an amino acid sequence at least 95% identical to SEQ ID NO: 1.

In some aspects, the enzyme further comprises a heterologous peptide segment, such as an XTEN peptide, an IgG Fc, an albumin, or an albumin binding peptide. In some aspects, the enzyme is coupled to polyethylene glycol (PEG). In some aspects, the enzyme is coupled to PEG via one or more lysine or cystine residues.

In some aspects, the MTase polypeptide is conjugated to an antibody, such as an scFv antibody. The antibody or scFv antibody may be an anti-MUC1 antibody, an anti-HER2 antibody, an anti-CTLA4 antibody, an anti-PD1 antibody, or an anti-PDL1 antibody.

The patient may be any animal, such as a mouse. For example, the patient may be a mammal, particularly a primate, and more particularly a human patient.

In some aspects, the tumor is a solid tumor. In some aspects, the tumor is a hematological tumor. In some aspects, the tumor is an osteosarcoma, a pancreatic cancer, a chordoma, a mesothelioma, a T-cell ALL, a glioma, a renal cell carcinoma, a melanoma, a squamous cell carcinoma, a gallbladder cancer, a gastric cancer, or a hepatocellular carcinoma.

In some aspects, the tumor has decreased levels of MTAP. In certain aspects, the tumor has an MTAP deletion. In some aspects, the tumor has an increased level of CD73 relative to a reference sample. In some aspects, the tumor has an increased level of CD73 and, optionally, a decreased level of MTAP relative to a reference level. In some aspects, the tumor has an increased level of CD39 relative to a reference sample. In some aspects, the tumor has an increased level of MTA relative to a reference level. In some aspects, the tumor has an increased level of ADO relative to a reference level. In some aspects, the reference level is a level in a healthy tissue in the patient. In some aspects, the reference level is a level in a healthy subject.

In some aspects, the patient has previously been treated for cancer and the enzyme is administered to prevent the recurrence of cancer. In some aspects, the method is a method of preventing metastasis. In some aspects, the method is a method for increasing sensitivity to immunotherapy. In some aspects, the patient has previously failed to respond to the administration of an immune checkpoint inhibitor. In some aspects, the method further comprises administering at least a second anti-cancer therapy to the subject. In some aspects, the second anti-cancer therapy is an immune checkpoint blockade, an adoptive T cell therapy, a surgical therapy, chemotherapy, radiation therapy, cryotherapy, hormone therapy, immunotherapy or cytokine therapy. In some aspects, the second anticancer therapy comprises an adoptive T cell therapy, an anti-PD1 antibody, an anti-CTLA-4 antibody, and/or an anti-PD-L1 antibody. In certain aspects, the anti-PD-L1 antibody comprises atezolizumab, avelumab, durvalumab, BMS-036559, or CK-301. In certain aspects, the anti-PD1 antibody comprises nivolumab, pembrolizumab, pidilizumab, AMP-223, AMP-514, cemiplimab, or PDR-001. In certain aspects, the anti-CTLA-4 therapy comprises ipilimumab or tremelimumab.

Certain aspects of the present invention also contemplate methods of treatment by the administration of the native MTase peptide, the nucleic acid encoding the native MTase peptide in a gene therapy vector, the modified MTase peptide, the nucleic acid encoding the modified MTase in a gene therapy vector, or the formulation of the present invention, and in particular methods of treating tumor cells or subjects with cancer. The subject may be any animal, such as a mouse. For example, the subject may be a mammal, particularly a primate, and more particularly a human patient. In some embodiments, the method may comprise selecting a patient with cancer.

In some embodiments, the cancer is any cancer that is sensitive to MTA depletion. In one embodiment, the present invention contemplates a method of treating a tumor cell or a cancer patient comprising administering a formulation comprising such a polypeptide. In some embodiments, the administration occurs under conditions such that at least a portion of the cells of the cancer are killed. In another embodiment, the formulation comprises such a modified MTase with MTA-degrading activity at physiological conditions and further comprising an attached polyethylene glycol chain. In some embodiment, the formulation is a pharmaceutical formulation comprising any of the above discussed MTase variants and pharmaceutically acceptable excipients. Such pharmaceutically acceptable excipients are well known to those of skill in the art. All of the above MTase variants may be contemplated as useful for human therapy.

In a further embodiment, there may also be provided a method of treating a tumor cell comprising administering a formulation comprising a non-bacterial (mammalian, e.g., primate or mouse) modified MTase that has MTA-degrading activity or a nucleic acid encoding thereof.

In an in vivo application, treating a tumor cell includes contacting the nutrient medium for a population of tumor cells with the MTase. In this embodiment, the medium can be blood, lymphatic fluid, spinal fluid and the like bodily fluid where MTA-depletion is desired.

In accordance with certain aspects of the present invention, such a formulation containing the modified MTase can be administered intravenously, intradermally, intraarterially, intraperitoneally, intralesionally, intracranially, intraarticularly, intraprostaticaly, intrapleurally, intrasynovially, intratracheally, intranasally, intravitreally, intravaginally, intrarectally, intratumorally, intramuscularly, subcutaneously, subconjunctival, intravesicularlly, mucosally, intrapericardially, intraumbilically, intraocularly, orally, topically, by inhalation, infusion, continuous infusion, localized perfusion, via a catheter, via a lavage, in lipid compositions (e.g., liposomes), or by other method or any combination of the forgoing as would be known to one of ordinary skill in the art.

In one embodiment, a composition comprising a modified MTase or a nucleic acid encoding a modified MTase is provided for use in the treatment of a tumor in a subject. In another embodiment, the use of a modified MTase or a nucleic acid encoding a modified MTase in the manufacture of a medicament for the treatment of a tumor is provided. Said modified MTase may be any modified MTase of the embodiments.

In one embodiment, methods are provided for selecting a patient having a tumor for treatment with a combined effective amount of an MTase polypeptide and an immune checkpoint inhibitor, the method comprising (a) determining whether the patient's tumor has a decreased level of MTAP, an increased level of CD73, an increased level of CD39, an increased level of MTA, or an increased level of ADO relative to a reference level, and (b) selecting the patient for treatment if the patient's tumor has a decreased level of MTAP, an increased level of CD73, an increased level of CD39, an increased level of MTA, or an increased level of ADO relative to a reference level, wherein the MTase polypeptide comprises a sequence having at least 90% identity to SEQ ID NO: 1 or 3, wherein the MTase polypeptide has MTase activity.

In some aspects, the methods further comprise administering a combined effective amount of an MTase polypeptide and an immune checkpoint inhibitor to the selected patient. In some aspects, the methods further comprise selecting the patient for treatment if the patient has previously failed to respond to the administration of an immune checkpoint inhibitor. In some aspects, the patient has previously undergone at least one round of anti-cancer therapy.

In one embodiment, methods are provided for treating a patient having severe combined immunodeficiency (SCID), the method comprising administering to the subject an effective amount of a pharmaceutical formulation comprising an MTase polypeptide in a pharmaceutically acceptable carrier, wherein the MTase polypeptide comprises a sequence having at least 90% identity to SEQ ID NO: 1 or 3, wherein the MTase polypeptide has MTase activity. In some aspects, the patient is selected for treatment if the patient has at least one mutation in an adenosine deaminase gene.

In one embodiment, methods are provided for selecting a patient having SCID for treatment with an effective amount of a pharmaceutical formulation comprising an MTase polypeptide in a pharmaceutically acceptable carrier, the method comprising (a) determining whether the patient has at least one mutation in an adenosine deaminase gene, and (b) selecting the patient for treatment if the patient has at least one mutation in an adenosine deaminase gene, wherein the MTase polypeptide comprises a sequence having at least 90% identity to SEQ ID NO: 1 or 3, wherein the MTase polypeptide has MTase activity. In some aspects, the methods further comprise administering an effective amount of an MTase polypeptide in a pharmaceutically acceptable carrier to the selected patient.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding," with reference to a nucleic acid, are used to make the invention readily understandable by the skilled artisan; however, these terms may be used interchangeably with "comprise" or "comprising," respectively.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A-B. FIG. 5A—Proliferation of murine CD8+ T cells as a function of MTA concentration in the presence or absence of MTA degrading enzymes. FIG. 5B—Proliferation of murine CD4+ T cells as a function of MTA in the presence or absence of MTA degrading enzymes. Numbers reported in each panel are the percent viable cells remaining at the end of the experiment.

FIGS. 6A-B. FIG. 6A—Growth of L1210 murine leukemia tumors treated with PEG-se-MTAN or PBS vehicle control. Closed circles represent "Vehicle control." Closed squares represent "PEG-se-MTAN." FIG. 6B—Kaplan-Meier plot of survival of treated and untreated mice (p<0.0035). Solid line represents "Vehicle control." Dashed line represents "PEG-se-MTAN."

FIGS. 7A-F. Assessment of lymphocyte subtypes from tumors and TDLNs of L1210 leukemia allografts treated with PEG-se-MTAN. FIG. 7A—Percent TCRβ+ in CD45+ viable cells in tumors. FIG. 7B—Percent CD4+Ki67+ in tumors. FIG. 7C—Percent CD8+Ki67+ in tumors. FIG. 7D—Percent TCRβ+ in all cells in TDLNs. FIG. 7E—Percent CD11b+ in TDLNs. FIG. 7F—Percent F4/80+ in TDLNs.

FIGS. 8A-B. Efficacy of PEG-hs-MTAP in the B16 WT and B16-MTAP$^{-/-}$ melanoma tumor models. FIG. 8A—B16-F10 growth. FIG. 8B—B16-MTAP KO growth.

FIG. 9A—Percent of CD4+ cells in TCRβ+ cells. FIG. 9B—Percent of TCRβ-, NK1.1+ in CD45+. FIG. 9C—Percent of CD8+/Granzyme B+ that are Ki67+.

FIG. 10A—Tumor growth following treatment with either vehicle, PEG-MTAN (50 mg/kg), anti-CTLA4 (10 mg/kg, clone UC10-4F10-11, Bio X Cell), or the combination of PEG-MTAN/anti-CTLA4. FIG. 10B—Lung metastases following treatment with either vehicle, PEG-MTAN (50 mg/kg), anti-CTLA4 (10 mg/kg, clone UC10-4F10-11, Bio X Cell), or the combination of PEG-MTAN/anti-CTLA4.

DETAILED DESCRIPTION

Figure 1:
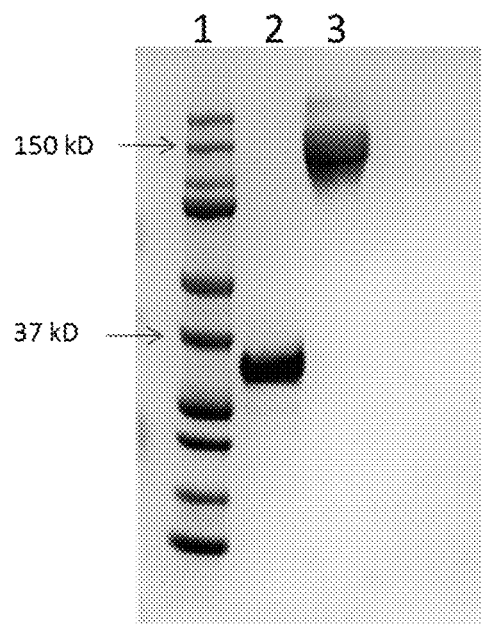
FIG. 1. SDS-PAGE of Precision Plus protein MW standard (Biorad; Lane 1), purified hs-MTAP (Lane 2), and PEG 5,000 MW modified hs-MTAP (Lane 3).

The present invention discloses the use of enzymes for the specific depletion of MTA and/or ADO in the tumor microenvironment and/or in the blood. MTA/ADO depleting enzymes are used to lower MTA/ADO concentrations for the treatment of tumors with MTAP deletions or promoter repressed MTAP thus preventing tumor mediated tolerogenic effects and instead mediating tumor ablating pro-inflammatory responses. MTA/ADO depleting enzymes are also used for the treatment of cancer patients whose tumors express increased amounts of CD39 and/or CD73 or SCID patients whose disease is associated with mutations in the adenosine deaminase gene. As such, the present invention provides methods of using therapeutic enzymes that degrade MTA/ADO to treat diseases, such as cancer or SCID caused by mutations in adenosine deaminase. These methods remove MTA/ADO from the tumor microenvironment and/or from circulation.

I. DEFINITIONS

As used herein the terms "protein" and "polypeptide" refer to compounds comprising amino acids joined via peptide bonds and are used interchangeably.

As used herein, the term "fusion protein" refers to a chimeric protein containing proteins or protein fragments operably linked in a non-native way.

As used herein, the term "half-life" (½-life; $T_{1/2}$) refers to the time that would be required for the concentration of a polypeptide thereof to fall by half in vitro or in vivo, for example, after injection in a mammal.

The terms "in operable combination," "in operable order," and "operably linked" refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

The term "linker" is meant to refer to a compound or moiety that acts as a molecular bridge to operably link two different molecules, wherein one portion of the linker is operably linked to a first molecule, and wherein another portion of the linker is operably linked to a second molecule.

The term "PEGylated" refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymers of PEG and amino acids have been explored as novel biomaterial that would retain the biocompatibility of PEG, but that would have the added advantage of numerous attachment points per molecule (thus providing greater drug loading), and that can be synthetically designed to suit a variety of applications.

The term "gene" refers to a DNA sequence that comprises control and coding sequences necessary for the production of a polypeptide or precursor thereof. The polypeptide can be encoded by a full-length coding sequence or by any portion of the coding sequence so as the desired enzymatic activity is retained.

The term "native" refers to the typical form of a gene, a gene product, or a characteristic of that gene or gene product when isolated from a naturally occurring source. A native form is that which is most frequently observed in a natural population and is thus arbitrarily designated the normal or wild-type form. In contrast, the term "modified," "variant," or "mutant" refers to a gene or gene product that displays modification in sequence and functional properties (i.e., altered characteristics) when compared to the native gene or gene product.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term "therapeutically effective amount" as used herein refers to an amount of a therapeutic composition (such as a therapeutic polynucleotide and/or therapeutic polypeptide) that is employed in methods to achieve a therapeutic effect. The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, elimination of a tumor, or prevention of the formation of a tumor.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "$k_{cat}$" as used herein refers to the turnover number or the number of substrate molecules each enzyme site converts to product per unit time, and in which the enzyme is working at maximum efficiency. The term "$k_{cat}/K_M$" as used herein is the specificity constant, which is a measure of how efficiently an enzyme converts a substrate into product.

The term "MTase" refers to any enzyme that catalyzes the phosphorolysis or hydrolysis of MTA into methylthioribose-1'-phosphate (MTR-1'-P) or methylthioribose (MTR) and adenine as well as the phosphorolysis or hydrolysis of adenosine into ribose-1'-phosphate or ribose and adenine. For example, it includes primate forms of MTAP, or particularly, human forms of MTAP, as well as prokaryotic forms of MTAN.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an MTase.

"Subject" and "patient" refer to either a human or non-human, such as primates, mammals, and vertebrates. In particular embodiments, the subject is a human.

II. MTASE ENGINEERING

Humans have an enzyme called methylthioadenosine phosphorylase (MTAP) whose functions is to catalyze the conversion of methylthioadenosine (MTA), a byproduct of polyamine synthesis, into methylthioribose-1'-phosphate (MTR-1'-P) and adenine. Prokaryotes have an enzyme called methylthioadenosine nucleosidase (MTAN), which functions to catalyze the conversion of methylthioadenosine (MTA), a byproduct of polyamine synthesis, into methylthioribose (MTR) and adenine. These enzymes are also capable of degrading adenosine (ADO).

Some embodiments concern modified proteins and polypeptides. Particular embodiments concern a modified protein or polypeptide that exhibits at least one functional activity that is comparable to the unmodified version, preferably, the MTA/ADO-degrading activity. In further aspects, the protein or polypeptide may be further modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide, such as the MTA/ADO-degrading activity. In certain embodiments, the unmodified protein or polypeptide is a native MTase, preferably a human MTase. Due to the undesired effects of immunogenicity seen clinically with the use of non-human protein therapeutics, the inventors sought to engineer therapeutically relevant MTA/ADO-degrading activity into a human enzyme (i.e., engineer an enzyme with high $k_{cat}$ and low $K_M$ values for MTA/ADO and also displaying a favorable specificity). It is specifically contemplated that embodiments concerning a "modified protein" may be implemented with respect to a "modified polypeptide," and vice versa.

Determination of activity may be achieved using assays familiar to those of skill in the art, particularly with respect to the protein's activity, and may include for comparison purposes, for example, the use of native and/or recombinant versions of either the modified or unmodified protein or polypeptide. For example, the MTA/ADO-degrading activity may be determined by any assay to detect the products resulting from the degradation of MTA/ADO, such as the detection of adenine.

In certain embodiments, a modified polypeptide, such as a modified MTase, may be identified based on its increase in MTA/ADO-degrading activity. For example, substrate recognition sites of the unmodified polypeptide may be identified. This identification may be based on structural analysis or homology analysis. A population of mutants involving modifications of such substrate recognitions sites may be generated. In a further embodiment, mutants with increased MTA/ADO-degrading activity may be selected from the mutant population. Selection of desired mutants may include methods for the detection of byproducts or products from MTA/ADO degradation.

Modified proteins may possess deletions and/or substitutions of amino acids; thus, a protein with a deletion, a protein with a substitution, and a protein with a deletion and a substitution are modified proteins. In some embodiments, these modified proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A modified protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

III. ENZYMATIC ADO/MTA DEGRADATION FOR THERAPY

In certain aspects, the polypeptides may be used for the treatment of diseases, such as cancer or SCID, with enzymes that deplete MTA/ADO. As such, provided herein are treatment methods using MTase with MTA/ADO-degrading activity. In some embodiments, provided herein are enzymes with MTA/ADO-degrading activity for increased therapeutic efficacy. An anti-cancer response may be inhibiting tumor growth, inducing tumor cell death, tumor regression, preventing or delaying tumor recurrence, tumor growth, tumor spread, or tumor elimination.

Certain aspects of the present invention provide a modified MTase with MTA/ADO-degrading activity for treating diseases, such as tumors or SCID. In one example, the modified polypeptide may have human polypeptide sequences and thus may prevent allergic reactions in human patients, allow repeated dosing, and increase the therapeutic efficacy.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, gallbladder, skin, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, gallbladder cancer, breast cancer, colon cancer, colorectal cancer, endometrial or uterine carcinoma, salivary gland carcinoma, kidney or renal cancer, renal cell carcinoma, prostate cancer, vulval cancer, thyroid cancer, various types of head and neck cancer, head and neck squamous cell carcinoma, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The MTase may be used herein as an antitumor agent in a variety of modalities for depleting MTA/ADO from a tumor cell, tumor tissue, or the circulation of a mammal with cancer, or for depletion of MTA/ADO where its depletion is considered desirable. In addition, the MTase may be used as a treatment for SCID associated with adenosine deaminase mutations for depleting ADO from the circulation of a mammal with SCID.

Depletion can be conducted in vivo in the circulation of a mammal, in vitro in cases where MTA/ADO depletion in tissue culture or other biological mediums is desired, and in ex vivo procedures where biological fluids, cells, or tissues are manipulated outside the body and subsequently returned to the body of the patient mammal. Depletion of MTA/ADO from circulation, culture media, biological fluids, or cells is conducted to reduce the amount of MTA/ADO accessible to the material being treated, and therefore comprises contacting the material to be depleted with a MTA/ADO-degrading amount of the MTase under MTA/ADO-degrading conditions as to degrade the ambient MTA/ADO in the material being contacted.

MTA/ADO-degrading efficiency can vary widely depending upon the application, and typically depends upon the amount of MTA/ADO present in the material, the desired rate of depletion, and the tolerance of the material for exposure to MTase. MTA/ADO levels in a material, and therefore rates of MTA/ADO depletion from the material, can readily be monitored by a variety of chemical and biochemical methods well known in the art. Exemplary MTA/ADO-degrading amounts are described further herein, and can range from 0.001 to 100 units (U) of MTase, preferably about 0.01 to 10 U, and more preferably about 0.1 to 5 U MTase per milliliter (mL) of material to be treated.

MTA/ADO-degrading conditions are buffer and temperature conditions compatible with the biological activity of an MTase enzyme, and include moderate temperature, salt, and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

In one embodiment, the contacting in vivo is accomplished by administering, by intravenous or intraperitoneal injection, a therapeutically effective amount of a physiologically tolerable composition comprising an MTase to a patient, thereby depleting the circulating MTA/ADO present in the patient.

A therapeutically effective amount of an MTase is a predetermined amount calculated to achieve the desired effect, i.e., to deplete MTA/ADO in a patient's circulation. Thus, the dosage ranges for the administration of an MTase are those large enough to produce the desired effect. The dosage should not be so large as to cause adverse side effects, such as hyperviscosity syndromes, pulmonary edema, congestive heart failure, and the like. Generally, the dosage will vary with age of, condition of, sex of, and extent of the disease in the patient and can be determined by one of skill in the art. The dosage can be adjusted by the individual physician in the event of any complication.

For example, a therapeutically effective amount of an MTase may be an amount such that when administered in a physiologically tolerable composition is sufficient to achieve a intravascular (plasma) or local concentration of from about 0.001 to about 100 units (U) per mL, preferably above about 0.1 U, and more preferably above 1 U MTase per mL. Typical dosages can be administered based on body weight, and are in the range of about 5-1000 U/kilogram (kg)/day, preferably about 5-100 U/kg/day, more preferably about 10-50 U/kg/day, and more preferably about 20-40 U/kg/day.

The MTase can be administered parenterally by injection or by gradual infusion over time. The MTase can be administered intravenously, intraperitoneally, orally, intramuscularly, subcutaneously, intracavity, transdermally, dermally, can be delivered by peristaltic means, can be injected directly into the urinary tract, or can be administered by a pump connected to a catheter that may contain a potential biosensor for MTA/ADO.

The therapeutic compositions containing MTase are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the enzyme, and degree of therapeutic effect desired. Precise amounts of enzyme required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of MTase and conversely low serum and tissue levels of MTA/ADO. Alternatively, continuous intravenous infusion sufficient to maintain concentrations in the blood in the ranges specified for in vivo therapies are contemplated.

IV. CONJUGATES

Compositions and methods of the present invention involve modified MTases, such as by forming conjugates with heterologous peptide segments or polymers, such as polyethylene glycol. In further aspects, the MTases may be linked to PEG to increase the hydrodynamic radius of the enzyme and hence increase the serum persistence. In certain aspects, the disclosed polypeptide may be conjugated to any targeting agent, such as a ligand having the ability to specifically and stably bind to an external receptor or binding site on a target cell (e.g., U.S. Patent Publ. 2009/0304666).

A. Fusion Proteins

Certain embodiments of the present invention concern fusion proteins. These molecules may have a modified MTase linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the MTase may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

Fusion protein modifications of MTase may be formed with cell-targeting moieties, for example, an antibody, a growth factor, a hormone, a peptide, an aptamer or a cytokine. For instance, a cell targeting moiety according the embodiments may bind to a skin cancer cell such as a melanoma cell. It has been demonstrated that the gp240 antigen is expressed in a variety of melanomas but not in normal tissues. Thus, in certain aspects of the embodiments, there is provided a cell targeting construct comprising an MTase and a cell-targeting moiety that binds to gp240. In some instances, the gp240 binding molecule may be an antibody, such as the ZME-018 (225.28) antibody or the 9.2.27 antibody. In an even more preferred embodiment, the gp240 binding molecule may be a single chain antibody such as the scFvMEL antibody. Therefore, in a very specific embodiment of the invention, there is provided a cell targeting construct comprising MTase conjugated to scFvMEL.

In yet further specific embodiments of the invention, cell targeting constructs may be directed to breast cancer cells. For example, cell targeting moieties that bind to Her-2/neu, such as anti-Her-2/neu antibodies may conjugated to MTase. One example of such a cell targeting construct is a fusion protein comprising the single chain anti-Her-2/neu antibody scFv23 and MTase. Other scFv antibodies such as scFv (FRP5) that bind to Her-2/neu may also be used in the compositions and methods of the current embodiments (von Minckwitz et al., 2005).

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Other examples are the cell targeting agents described in U.S. patent application no. 2004/005647 and in Winthrop et al., 2003 that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy.

In certain additional embodiments, it is envisioned that immune checkpoint blockade inhibitors can be used to form fusions with MTase. For example, an antibody, or fragment thereof (e.g., an scFv) that is antagonistic to PD-1, PDL-1, or PDL-2 (e.g., antibodies described in U.S. Pat. Nos. 8,735,553, 8,354,509, and 8,008,449; PCT Appln. Nos. WO2009/101611 and WO2009/114335) may be fused to MTase. In another example, an antibody, or fragment thereof (e.g., an scFc) that recognizes CTLA-4 (e.g., U.S. Pat. No. 8,119,129 and PCT Appln. Nos. WO 01/14424, WO 98/42752, and WO 00/37504) may be fused to MTase. Further checkpoint blockade molecules are discussed below.

B. Linkers

In certain embodiments, the MTase may be chemically conjugated using bifunctional cross-linking reagents or fused at the protein level with peptide linkers.

Bifunctional cross-linking reagents have been extensively used for a variety of purposes, including preparation of affinity matrices, modification and stabilization of diverse structures, identification of ligand and receptor binding sites, and structural studies. Suitable peptide linkers may also be used to link the MTase, such as Gly-Ser linkers.

Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidine-, indole-, carboxyl-specific groups. Of these, reagents directed to free amino groups have become especially popular because of their commercial availability, ease of synthesis, and the mild reaction conditions under which they can be applied.

A majority of heterobifunctional cross-linking reagents contain a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling, in one example, of aldehydes to free thiols. The cross-linking reagent can be modified to cross-link various functional groups.

Additionally, any other linking/coupling agents and/or mechanisms known to those of skill in the art may be used to combine an MTase, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed in accordance herewith. Other useful cross-linkers, not considered to contain or generate a protected disulfide, include SATA, SPDP, and 2-iminothiolane (Wawrzynczak and Thorpe, 1987). The use of such cross-linkers is well understood in the art. Another embodiment involves the use of flexible linkers.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation, or high performance liquid chromatography, will generally be of most use. Other chromatographic techniques, such as Blue-Sepharose separation, may also be used. Conventional methods to purify the fusion proteins from inclusion bodies may be useful, such as using weak detergents, such as sodium N-lauroyl-sarcosine (SLS).

C. PEGylation

In certain aspects of the invention, methods and compositions related to PEGylation of an MTase are disclosed. For example, the MTase may be PEGylated in accordance with the methods disclosed herein.

PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homodimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70% active, the amount of PEG used should ensure that only active PEG molecules are counted in the protein-to-PEG reaction stoichiometry.

V. PROTEINS AND PEPTIDES

In certain embodiments, the present invention concerns novel compositions comprising at least one protein or peptide, such as an MTase. These peptides may be comprised in a fusion protein or conjugated to an agent as described supra.

As used herein, a protein or peptide generally refers, but is not limited to, a protein of greater than about 200 amino acids, up to a full-length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide, and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). The coding regions for known genes may be amplified and/or expressed using the techniques disclosed herein or as would be known to those of ordinary skill in the art. Alternatively, various commercial preparations of proteins, polypeptides, and peptides are known to those of skill in the art.

VI. NUCLEIC ACIDS AND VECTORS

In certain aspects of the invention, nucleic acid sequences encoding an an MTase or a fusion protein containing an MTase may be disclosed. Depending on which expression system is used, nucleic acid sequences can be selected based on conventional methods. For example, if the MTase is derived from primate MTAP or prokaryotic MTAN and contains multiple codons that are rarely utilized in *E. coli*, then that may interfere with expression. Therefore, the respective genes or variants thereof may be codon optimized for *E. coli* expression. Various vectors may be also used to express the protein of interest, such as an MTase. Exemplary vectors include, but are not limited, plasmid vectors, viral vectors, transposon, or liposome-based vectors.

VII. HOST CELLS

Host cells may be any that may be transformed to allow the expression and secretion of an MTase and conjugates thereof. The host cells may be bacteria, mammalian cells, yeast, or filamentous fungi. Various bacteria include *Escherichia* and *Bacillus*. Yeasts belonging to the genera *Saccharomyces, Kiuyveromyces, Hansenula,* or *Pichia* would find use as an appropriate host cell. Various species of filamentous fungi may be used as expression hosts, including the following genera: *Aspergillus, Trichoderma, Neurospora, Penicillium, Cephalosporium, Achlya, Podospora, Endothia, Mucor, Cochliobolus,* and *Pyricularia*.

Examples of usable host organisms include bacteria, e.g., *Escherichia coli* MC1061, derivatives of *Bacillus subtilis* BRB1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22 (Mellor et al., 1983) or *Schizosaccharomyces pombe*; and filamentous fungi, e.g., *Aspergillus nidulans, Aspergillus awamori* (Ward, 1989), or *Trichoderma reesei* (Penttila et al., 1987; Harkki et al., 1989).

Examples of mammalian host cells include Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCCCRL 1548), SV40-transformed monkey kidney cells (COS-1; ATCC CRL 1650), and murine embryonic cells (NIH-3T3; ATCC CRL 1658). The foregoing being illustrative but not limitative of the many possible host organisms known in the art. In principle, all hosts capable of secretion can be used whether prokaryotic or eukaryotic.

Mammalian host cells expressing the MTase and/or their fusion proteins are cultured under conditions typically employed to culture the parental cell line. Generally, cells are cultured in a standard medium containing physiological salts and nutrients, such as standard RPMI, MEM, IMEM, or DMEM, typically supplemented with 5%-10% serum, such as fetal bovine serum. Culture conditions are also standard, e.g., cultures are incubated at 37° C. in stationary or roller cultures until desired levels of the proteins are achieved.

VIII. PROTEIN PURIFICATION

Protein purification techniques are well known to those of skill in the art. These techniques involve, at one level, the homogenization and crude fractionation of the cells, tissue, or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulphate, PEG, antibodies and the like, or by heat denaturation, followed by centrifugation; chromatography steps, such as ion exchange, gel filtration, reverse phase, hydroxyapatite, and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified, for example, an MTase, a fusion protein containing the MTase, or an MTase post-PEGylation. For example, a His tag or an affinity epitope may be comprised in such an MTase to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

IX. PHARMACEUTICAL COMPOSITIONS

It is contemplated that an MTase can be administered systemically or locally. They can be administered intravenously, intrathecally, and/or intraperitoneally.

It is not intended that the present invention be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Generally, pharmaceutical compositions may comprise an effective amount of one or more MTase or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one MTase isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of a composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition that includes MTase, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the MTase or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

X. COMBINATION TREATMENTS

In certain embodiments, the compositions and methods of the present embodiments involve administration of an MTase in combination with a second or additional therapy. The methods and compositions, including combination therapies, enhance the therapeutic or protective effect, and/or increase the therapeutic effect of another therapy. Therapeutic and prophylactic methods and compositions can be provided in a combined amount effective to achieve the desired effect. This process may involve administering both an MTase and a second therapy. A tissue, organ, or cell can be exposed to one or more compositions or pharmacological formulation(s) comprising one or more of the agents (i.e., an MTase or a second agent), or by contacting the tissue, organ, and/or cell with two or more distinct compositions or formulations, wherein one composition provides 1) an MTase, 2) a second agent, or 3) both an MTase and a second agent. Also, it is contemplated that such a combination therapy can be used in conjunction with surgical therapy.

The terms "contacted" and "exposed," when applied to a cell, are used herein to describe the process by which a therapeutic construct is delivered to a target organ or are placed in direct juxtaposition with the target cell.

An MTase may be administered before, during, after, or in various combinations relative to a second treatment. The administrations may be in intervals ranging from concurrently to minutes to days to weeks. In embodiments where the MTase is provided to a patient separately from a second agent, one would generally ensure that a significant period of time did not expire between the time of each delivery, such that the two treatments would still be able to exert an advantageously combined effect on the patient. In such instances, it is contemplated that one may provide a patient with the MTase and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that the MTase may be given on any day of day 1 to day 90 (this such range includes intervening days) or any combination thereof, and another treatment is given on any day of day 1 to day 90 (this such range includes intervening days) or any combination thereof. Within a single day (24-hour period), the patient may be given one or multiple administrations of the treatment(s). Moreover, after a course of treatment, it is contemplated that there is a period of time at which no treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an MTase is "A" and a second therapy is "B":

| A/B/A B/A/B B/B/A A/A/B A/B/B B/A/A A/B/B/B B/A/B/B |
|---|
| B/B/B/A B/B/A/B A/A/B/B A/B/A/B A/B/B/A B/B/A/A |
| B/A/B/A B/A/A/B A/A/A/B B/A/A/A A/B/A/A A/A/B/A |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaII); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum;

etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as 7-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, Nat Rev Cancer, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) *Proc Natl Acad Sci USA* 95(17): 10067-10071; Camacho et al. (2004) *J Clin Oncology* 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

In some embodiment, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering (Park, Rosenberg et al. 2011). Isolation and transfer of tumor specific T cells has been shown to be successful in treating melanoma. Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors (Jena, Dotti et al. 2010).

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

XI. KITS

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of an MTase, optionally formulated as a pharmaceutical, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes an MTase that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

XII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Gene Construction, Expression, and Purification of MTAP from Homo sapiens A gene for expression of the MTAP enzyme from *Homo sapiens* (hs-MTAP; SEQ ID NO: 1) was constructed by overlap extension polymerase chain reaction (PCR) of an *E. coli* codon-optimized gene block designed using IDT software. The full-length gene includes an N-terminal NcoI restriction-enzyme site, an N-terminal $His_6$ tag, an *E. coli* codon-optimized hs-MTAP gene, a stop codon, and a C-terminal EcoRI restriction-enzyme site. The aforementioned restriction-enzyme sites were used to clone the assembled gene into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an $OD_{600}$ 1.0 was reached by adding IPTG (0.5 mM final concentration) with continued shaking overnight at 37° C. Cells were then harvested by centrifugation and re-suspended in lysis buffer consisting of 50 mM sodium phosphate (pH 7.4), 300 mM NaCl, 1 mM phenylmethylsulfonylfluoride, and 1 µg/mL DNase. Lysis was achieved by French press, and the lysate was cleared of particulates by centrifuging at 20,000×g for 1 h at 4° C. The supernatant was then filtered through a 5 µm syringe filter and applied to a Ni-NTA/agarose column (Qiagen) pre-equilibrated in 50 mM sodium phosphate (pH 7.4), 300 mM NaCl buffer. After loading the lysate onto the column, the resin was washed with 5 column volumes (CV) of 50 mM sodium phosphate (pH 7.4), 300 mM NaCl, 20 mM imidazole buffer. Next the flow rate was set to slowly wash the column with 100 CV of endotoxin-free PBS (Corning) containing 1% v/v Triton-X114 in order to remove any lipopolysaccharide (LPS or endotoxin), which is a typical contaminant of bacterial expression systems. The washed enzyme was then eluted in 5 CV of endotoxin-free PBS with 250 mM imidazole, and the resin was rinsed with a second 5 CV portion of endotoxin-free PBS. At this point, enzyme was buffer exchanged into fresh PBS to remove imidazole, and 10% glycerol was added. Aliquots were flash frozen in liquid nitrogen for storage at −80° C. Alternatively, enzyme was immediately buffer exchanged into freshly made, sterile 100 mM sodium phosphate (pH 8.4) to both remove imidazole and prepare it for PEGylation (as described in Example 3). Enzyme purities were typically >95% based on SDS-PAGE analysis, and typical yields averaged around 65 mg/L of culture. Protein quantities were assessed by measuring $Abs_{280\ nm}$ and using the calculated enzyme extinction coefficient of 29,950 $M^{-1}\ cm^{-1}$.

Example 2—Gene Construction, Expression, and Purification of MTAN from Salmonella enterica A gene for expression of the MTAN enzyme from *Salmonella enterica* (se-MTAN; SEQ ID NO: 3) was obtained by overlap extension polymerase chain reaction (PCR) of an *E. coli* codon-optimized gene block designed using software from IDT. The full-length gene includes an N-terminal NcoI restriction-enzyme site, an N-terminal $His_6$ tag, an *E. coli* codon-optimized se-MTAN gene, a stop codon, and a C-terminal EcoRI restriction-enzyme site. The aforementioned restriction-enzyme sites were used to clone the assembled gene into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an $OD_{600}$ ~1.0 was reached by adding IPTG (0.5 mM final concentration) with continued shaking overnight at 37° C. Cells were then harvested by centrifugation and re-suspended in lysis buffer consisting of 50 mM sodium phosphate (pH 7.4), 300 mM NaCl, 1 mM phenylmethylsulfonylfluoride, and 1 µg/mL DNase. Lysis was achieved by French press, and the lysate was cleared of particulates by centrifuging at 20,000×g for 1 h at 4° C. The supernatant was then filtered through a 5 µm syringe filter and applied to a Ni-NTA/agarose column (Qiagen) pre-equilibrated in 50 mM sodium phosphate (pH 7.4), 300 mM NaCl buffer. After loading the lysate onto the column, the resin was washed with 5 column volumes (CV) of 50 mM sodium phosphate (pH 7.4), 300 mM NaCl, 20 mM imidazole buffer. Next the flow rate was set to slowly wash the column with 100 CV of endotoxin-free PBS (Corning) containing 1% v/v Triton-X114 in order to remove any lipopolysaccharide (LPS or endotoxin), which is a typical contaminant of bacterial expression systems. The washed enzyme was then eluted in 5 CV of endotoxin-free PBS with 250 mM imidazole, and the resin was rinsed with a second 5 CV portion of endotoxin-free PBS. At this point, enzyme was buffer exchanged into fresh PBS to remove imidazole, and 10% glycerol was added. Aliquots were flash frozen in liquid nitrogen for storage at −80° C. Alternatively, enzyme was immediately buffer exchanged into freshly made, sterile 100 mM sodium phosphate pH 8.4 to both remove imidazole and prepare it for PEGylation (as described in Example 4). Enzyme purities were typically >5% based on SDS-PAGE analysis, and typical yields averaged around 70 mg/L of culture. Protein quantities were assessed by measuring $Abs_{280\ nm}$ and using the calculated enzyme extinction coefficient of 6,210 $M^{-1}$ $cm^{-1}$.

Example 3—Pharmacological Preparation of MTAP from *Homo sapiens*

To improve the circulation time of the human enzyme in vivo, the hydrodynamic radius of hs-MTAP was increased by functionalizing surface reactive groups in the protein by conjugation to PEG. In one embodiment, hs-MTAP was functionalized by reaction of surface lysine residues with Methoxyl PEG Succinimidyl Carbonate 5000 MW (NANOCS). The purified, endotoxin-free enzyme was thoroughly buffer exchanged into freshly prepared 100 mM sodium phosphate (pH 8.4) and concentrated to 5 mg/mL. The resulting solution was added directly to a 100:1 molar excess of solid PEG reagent and allowed to react at room temperature for 1 h (FIG. 1). Un-reacted PEG was removed from solution by thorough buffer exchange into fresh, endotoxin-free PBS in a 100 KDa cut-off centrifugal filtration device (Amicon). Endotoxin levels were quantified using the Chromo-LAL kinetic chromogenic endotoxin testing kit (Associates of Cape Cod, Inc.). Enzyme washed in the manner described above typically resulted in endotoxin levels <10 EU/mg of purified hs-MTAP.

Example 4—Pharmacological Preparation of MTAN from *Salmonella enterica*

Figure 2:
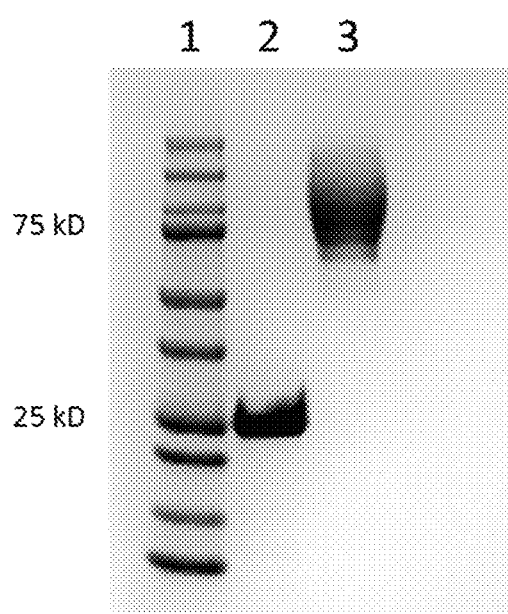
FIG. 2. SDS-PAGE of Precision Plus protein MW standard (Biorad; Lane 1), purified se-MTAN (Lane 2), and PEG 5,000 MW modified se-MTAN (Lane 3).

To improve circulatory residence time of the *Salmonella* enzyme in vivo, the hydrodynamic radius of se-MTAN was increased by functionalizing surface reactive groups in the protein by conjugation to PEG. In one embodiment, se-MTAN was functionalized by reaction of surface lysine residues with Methoxyl PEG Succinimidyl Carbonate 5000 MW (NOF Corporation). The purified, endotoxin free enzyme was thoroughly buffer exchanged into freshly prepared 100 mM sodium phosphate (pH 8.4) and concentrated to 5 mg/mL. The resulting solution was added directly to a 100:1 molar excess of solid PEG reagent and allowed to react at room temperature for 1 h (FIG. 2). Un-reacted PEG was removed from solution by thorough buffer exchange into fresh, endotoxin-free PBS in a 100 kDa cut-off filter (Amicon). Endotoxin levels were quantified using the Chromo-LAL kinetic chromogenic endotoxin testing kit (Associates of Cape Cod, Inc.). Enzyme washed in the manner described above typically resulted in endotoxin levels <10 EU/mg of purified se-MTAN.

Example 5—Assay for Measuring Kinetic Parameters of MTAP and MTAN

The kinetic parameters of se-MTAN and hs-MTAP were quantified by a spectrophotometric assay, in which the decay in the maximum absorbance of the enzyme substrate, MTA, was monitored as a function of time as described elsewhere (Singh et al., 2004). MTA solutions were prepared in PBS (pH 7.4) to result in final concentrations ranging from 6 µM to 200 µM. MTA has a change in extinction coefficient of 1,600 $M^{-1}$ $cm^{-1}$ from its MTAP/MTAN degradation product adenine at a $X_{max}$ at 275 nm, while the other products of the reactions, methylthioribose-1'-phosphate/methylthioribiose, do not appreciably absorb at 275 nm. Reactions were initiated by adding and rapidly mixing enzyme solutions (~10 nM final) with the substrate solutions and monitoring the loss of substrate MTA at 37° C. by measuring $Abs_{275}$ nm over time. The resulting data was processed and fitted to the Michaelis-Menten equation for determining kinetic constants. Under these conditions, the kinetics of the hs-MTAP enzyme was found to have a $k_{cat}/K_M$ of $1.0 \times 10^5$ $M^{-1}$ $s^{-1}$ and se-MTAN was found to have a $k_{cat}/K_M$ of $3.0 \times 10^5$ $M^{-1}$ $s^{-1}$.

Example 6—Kinetic Stability of Hs-MTAP and Se-MTAN

Figure 3:
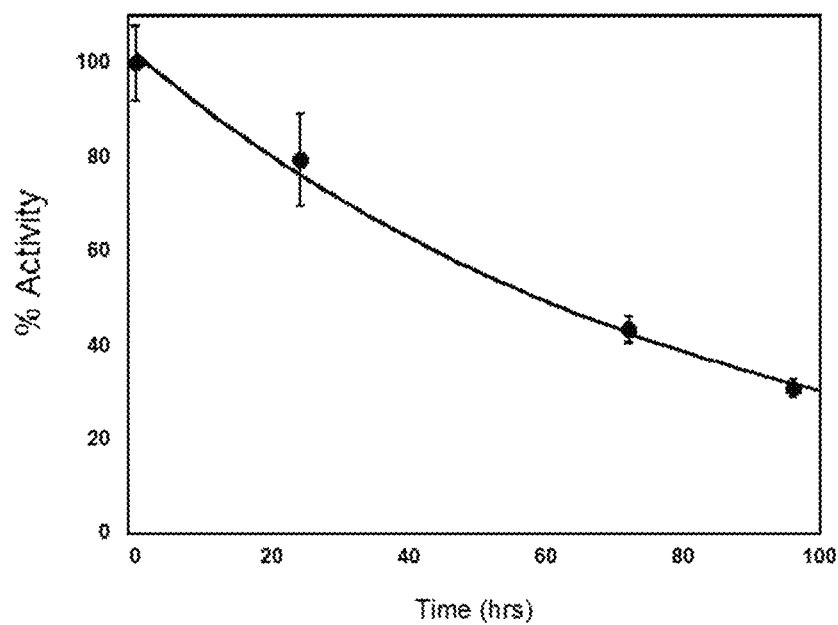
FIG. 3. Activity of hs-MTAP over time incubated in 100 mM phosphate buffer, pH 7.4 at 37° C., with a $T_{1/2}$ of 57 hrs.
Figure 4:
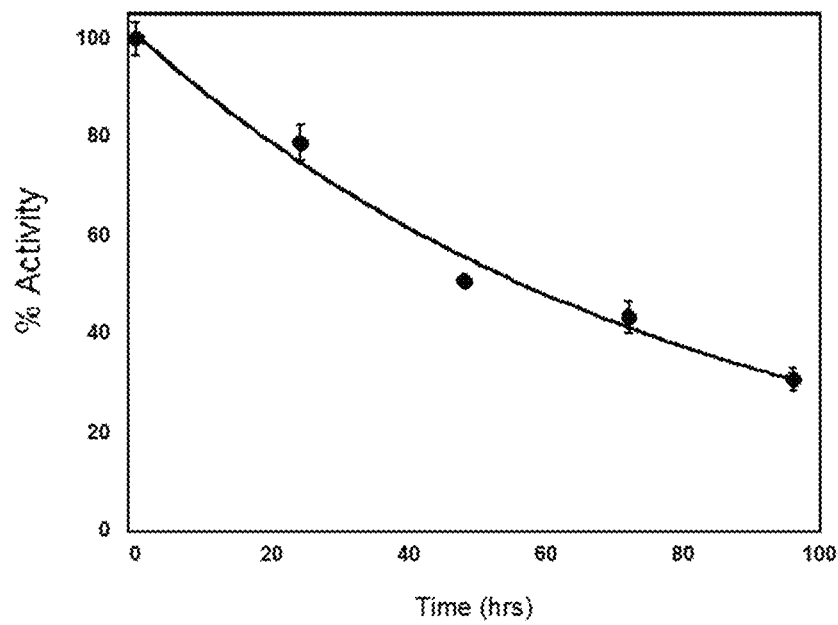
FIG. 4. Activity of se-MTAN over time incubated in 100 mM phosphate buffer, pH 7.4 at 37° C., with a $T_{1/2}$ of 56 hrs.

The kinetic stabilities of purified hs-MTAP and se-MTAN enzymes were determined by incubating the enzymes in a 100 mM phosphate buffer (pH 7.4) at 37° C. Over the course of four days, aliquots of hs-MTAP and se-MTAN were withdrawn from the incubations and assessed for their ability to degrade MTA as described in Example 5. The resulting data were processed and fitted to an exponential equation to determine the decay rate. Under these conditions, the hs-MTAP enzyme was found to have a half-life ($T_{1/2}$) of 57 hrs (FIG. 3) and se-MTAN was found to have a similar $T_{1/2}$ of 56 hrs (FIG. 4).

Example 7—Efficacy of Hs-MTAP and Se-MTAN in Restoring Proliferation of Murine T Cells Treated with MTA Spleens dissected from healthy 8-week-old C57BL6 mice were crushed in a 70 µm Falcon™ Cell Strainer to obtain single cells, which were further isolated using the EasySep™ Mouse T-Cell Isolation Kit (Stem Cell). Isolated T cells were brought to a concentration of $1 \times 10^6$ cells/mL in PBS and were processed according to the CellTrace™ Violet Cell Proliferation Kit protocol (Thermo Fisher), which measures proliferation as a function of dye dilution with each cell-division. The labeled cells were then re-counted and brought to $1 \times 10^6$ cells/mL of RPMI media and 1 mL/well were plated, after which anti-CD3/CD28 beads were added to activate the T cells (Dynabeads® Mouse T-Activator CD3/CD28 for T-Cell Expansion and Activation from Thermo Fisher) according to the protocol from the kit. Subsequently, three different MTA concentrations, 0 µM MTA, 125 µM MTA, or 250 µM MTA were added to the plated cells. Finally, MTAP and MTAN were added to the appropriate wells at a final concentration of 5 µM enzyme, and PBS was added to the control wells. After incubation for five days, cells were then collected and stained with anti- CD3, anti-CD4, anti-CD8, and Fixable Viability Dye eFluor™ 520 and analyzed by FACS. The antibodies used were all from Biolegend: PE anti-mouse CD3 (17A2), APC anti-mouse CD4 (GK1.5), APC/Fire™ 750 anti-mouse CD8a (53-6.7), and Brilliant Violet 421™ anti-mouse Ki-67 (16A8). Fixable Viability Dye eFluor™ 520 was purchased from Thermo Fisher.

Under these conditions, MTA potently inhibited the proliferation and viability of CD8+ T cells (FIG. 5A), and to a lesser extent CD4+ T cells (FIG. 5B), in a dose-dependent manner. This effect was completely reversed by addition of either hs-MTAP or se-MTAN (FIGS. 5A & 5B).

Example 8—Efficacy of PEG-Se-MTAN in the Autologous L1210 Mouse Leukemia Model

DBA/2 mice (n=17) were each inoculated with $5 \times 10^4$ cells of the highly aggressive L1210 murine leukemia cell line by subcutaneous flank injection. After allowing tumors to establish for an additional eight days (tumor mean=90 mm$^3$) the mice were split into two groups. The control group (n=8) was treated with PBS vehicle control by peri-tumoral injection every three days until tumors reached ≥2500 mm$^3$ in size. The experimental group (n=9) was treated in an identical manner except with 50 mg/kg of active PEG-se-MTAN by peri-tumoral injection every three days until tumors reached an endpoint of ≥2500 mm$^3$ in size. The growth rates of L1210 leukemia tumors were significantly retarded by 3.5-fold in the treatment group administered PEG-se-MTAN compared to the vehicle control group (FIG. 6A) resulting in a statistically significant life-span extension, p<0.0035 (FIG. 6B).

Example 9—MTAP-scFv and MTAN-scFV Fusion Proteins for Tumor Targeting

In some aspects, the present invention also contemplates polypeptides comprising the modified bacterial MTAN or mammalian MTAP linked to a heterologous amino acid sequence. For example, the native or modified MTAN/MTAP may be linked to a single-chain variable fragment (scFv) antibody that binds specific cell surface tumor antigens. In this embodiment, an scFv-MTAP/MTAN fusion protein with the scFv portion of the protein having specific affinity for a known tumor antigen, preferably a tumor specific antigen that internalizes at a slower rate, e.g., MUC-1, would allow the MTAN/MTAP portion of the fusion protein to be delivered to the tumor cell to degrade MTA. One example would be a scFv-MTAN/MTAP fusion protein where the scFv portion targets and binds to the human epidermal growth factor receptor 2 (HER2) that is upregulated in certain types of breast cancer. In this embodiment, a native or modified MTAN/MTAP-anti-HER2-scFV fusion protein would act to target and concentrate MTAN/MTAP directly to the tumor surface and act to degrade tumor produced MTA.

Example 10—MTAP- and MTAN-Anti-CTLA4-scFV Fusion Proteins

In some aspects, the present invention also contemplates polypeptides comprising the modified bacterial MTAN or mammalian MTAP linked to a heterologous amino acid sequence. For example, the native or modified MTAP/MTAN may be linked to a single-chain variable fragment (scFv) antibody that binds the Cytotoxic T-Lymphocyte Antigen 4 (CTLA-4) receptor on T-helper and T-regulatory cells. T-cells display the surface receptor CD28, which, when bound to its co-receptor, acts as a stimulatory signal for T-cell activation. In contrast, the surface receptor CTLA-4, when bound to its co-receptor, transmits an inhibitory signal to cytotoxic T-lymphocytes (CTLs) that down-regulates T-cell activation and prevents them from recognizing and attacking cancer cells. A blockade of CTLA-4 by an antagonizing antibody or antibody fragment allows the inhibitory T-cell signal to be reversed, allowing CD28 to continue to stimulate T-cell activation. In this embodiment a native or modified MTAP/MTAN-anti-CTLA4-scFV fusion protein would act to remove both inhibitory CTLA-4 signaling and inhibitory MTA signaling. In another embodiment, a native or modified MTAP/MTAN-anti-CTLA4-scFV fusion protein would act to remove both inhibitory CTLA-4 signaling and inhibitory ADO signaling. This embodiment of a native or modified MTAP/MTAN-anti-CTLA4-scFV fusion protein would be expected to potently upregulate T-cell activation and promote robust anti-tumoral responses.

Example 11—Assay for Measuring Kinetic Parameters of Adenosine by MTAP and MTAN

The kinetic parameters of se-MTAN and hs-MTAP were quantified by a spectrophotometric assay, in which the decay in the maximum absorbance of the enzyme substrate, adenosine (ADO), was monitored as a function of time. ADO solutions were prepared in PBS (pH 7.4) to result in final concentrations ranging from 6 μM to 800 PM. ADO has a change in extinction coefficient of 615 M$^{-1}$ cm$^{-1}$ from its MTAP/MTAN degradation product adenine at a $\lambda_{max}$ at 275 nm, while the other products of the reactions, ribose-1'-phosphate/ribose, do not appreciably absorb at 275 nm. Reactions were initiated by adding and rapidly mixing enzyme solutions (~20 nM final) with the substrate solutions and monitoring the loss of substrate MTA at 37° C. by measuring Abs$_{275}$ nm over time. The resulting data was processed and fitted to form of the Michaelis-Menten equation for determining kinetic constants. Under these conditions, the kinetics of the hs-MTAP enzyme was found to have a $k_{cat}/K_M$ of $5.0 \times 10^4$ M$^{-1}$ s$^{-1}$ and se-MTAN was found to have a $k_{cat}/K_M$ of $1.0 \times 10^5$ M$^{-1}$ s$^{-1}$.

Example 12—Effect of PEG-Se-MTAN on Immune Phenotype in the Autologous L1210 Mouse Leukemia Model Lymphocyte panels observed by FACS analyses from the tumors and tumor draining lymph nodes (TDLNs) of DBA/2 mice bearing L1210 allografts following three treatments of PEG-MTAN or vehicle control were assessed. PEG-MTAN administration resulted in large increases in the populations of tumor infiltrating lymphocytes (TILs) with greatly enhanced proliferation in CD4$^+$ and especially CD8$^+$ T cells consistent with the in vitro observations (FIGS. 7A-C). Very importantly, treated TDLNs also showed large increases in T cells and reduced populations of myeloid derived cells (FIGS. 7D-F) indicative of enhanced T cell activation.

Example 13—Construction of a B16 Melanoma MTAP Knockout Cell Line as a Model System As B16 is a very well characterized cell line in terms of metabolism and its interaction with host immune systems, it was hypothesized that an MTAP deletion in this strain would create a relevant model to evaluate the consequences of MTA accumulation both metabolically to the tumor and upon the host immune system. Cas9 protein (TrueCut™ Cas9 Protein v2) and synthetic single guide RNA purchased through ThermoFisher were transfected into B16-F10 WT cells using lypofectamine (Lipofectamine™ CRISPR-MAX™ Cas9 Transfection Reagent). After two days of transfection, cells were plated using limited dilution method into ten 96-well plates. Plates were examined daily for single cell clones and after reaching confluency (10-14 days post transfection) clones were further expanded and analyzed for MTAP expression through Western blotting, and clones lacking MTAP expression were verified for gene disruption by cloning and sequencing.

Figure 8B:
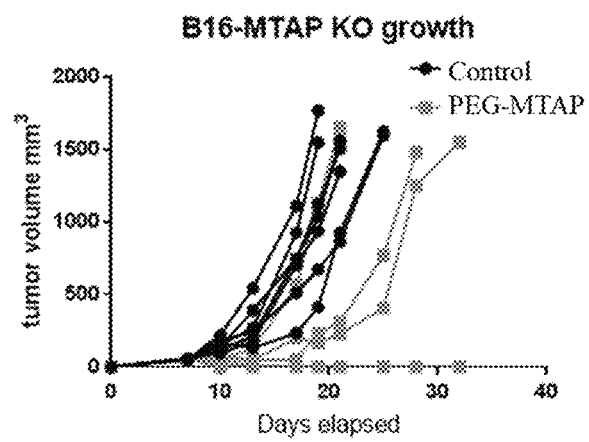

Example 14—Efficacy of PEG-Hs-MTAP in the B16 WT and B16-MTAP$^{-/-}$ Melanoma Tumor Models Two cohorts each of C57/BL6 mice were subcutaneously inoculated with either 50,000 WT B16-F10 or B16-F10 MTAP$^{-/-}$ cells. When the tumors reached a mean size of 55 mm$^3$ the mice were treated with either vehicle (PBS) or 50 mg/kg of PEG-MTAP three times/week by peri-tumoral injection for 2 weeks. As expected from a tumor highly expressing MTAP, it was observed that PEG-MTAP treatment had no effect on the growth of WT B16-F10 tumors (FIG. 8A). Administration of PEG-MTAP to B16-F10 MTAP$^{-/-}$ allografts however, drastically retarded tumor growth and resulted in complete responses (CRs) in 43% of the treatment group (3/7 CRs) (FIG. 8B).

Figure 9A:
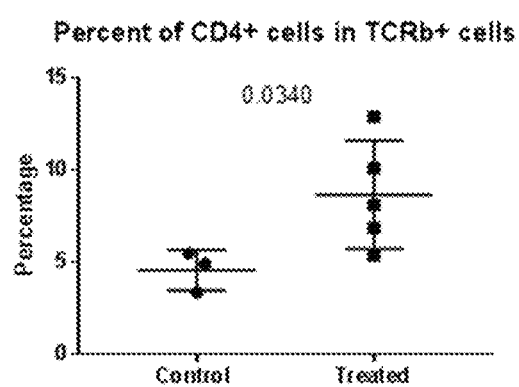
FIGS. 9A-C. Effect of PEG-hs-MTAP on immune phenotype in the B16-MTAP$^{-/-}$ melanoma tumor model.
Figure 9B:
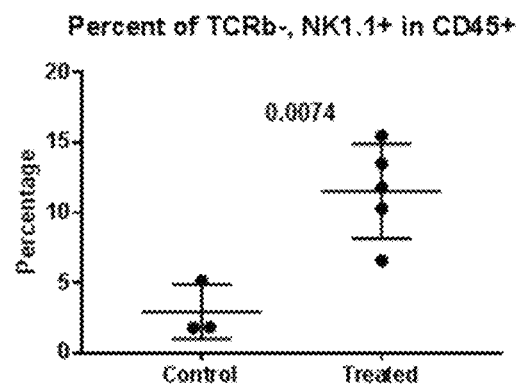
Figure 9C:
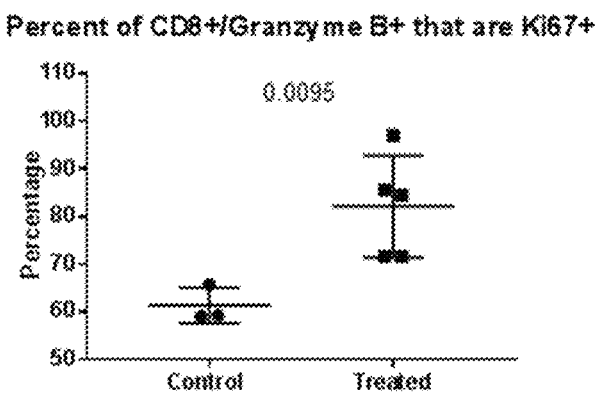

Example 15—Effect of PEG-Hs-MTAP on Immune Phenotype in the B16-MTAP-Melanoma Tumor Model Lymphocyte panels observed by FACS analyses from C57/BL6 mice bearing B16-F10 MTAP$^{-/-}$ tumor samples were assessed after treatment with two doses of PEG-MTAP or vehicle (analyzed 24 hr post dose). Treated groups exhibited large increases in the percentages of CD4$^+$ T cells and NK1.1$^+$ natural killer cells and large increases in the percentage of proliferating CD8+ Granzyme B+ T cells as compared to vehicle treated controls (FIGS. 9A-C).

Figure 10A:
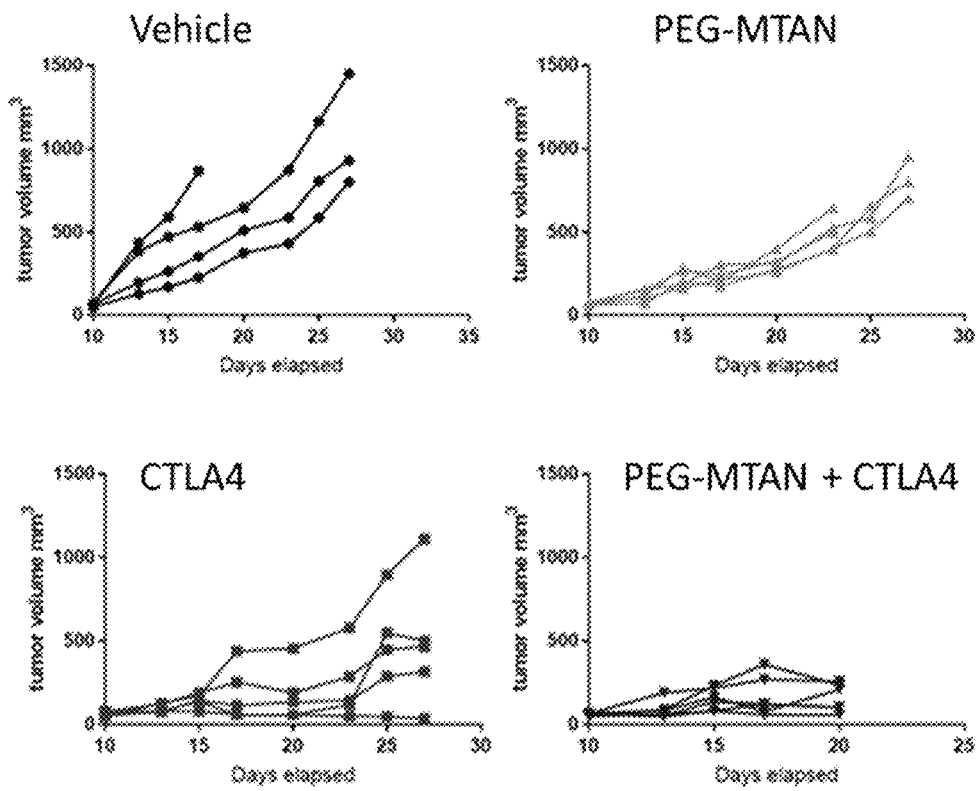
FIGS. 10A-B. Efficacy of PEG-MTAN/Anti-CTLA4 treatment of murine 4T1 breast carcinoma allografts.
Figure 10B:
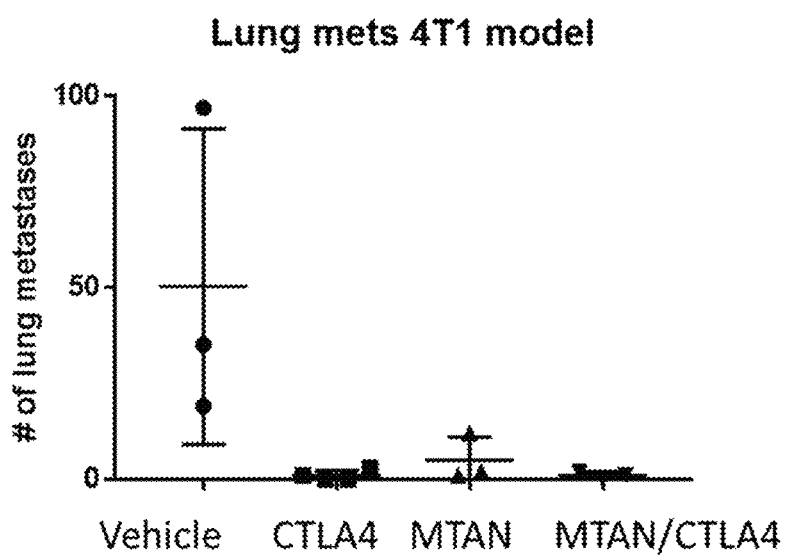

Example 16—Efficacy of PEG-MTAN/Anti-CTLA4 Treatment of Murine 4T1 Breast Carcinoma Allografts To assess the efficacy of controlling tumor growth by depletion of ADO and in combination with anti-CTLA4 immune checkpoint inhibition, four cohorts of BALB/C mice were inoculated with 50,000 4T1 cells in the mammary fat pad and allowed to establish tumors. 4T1 is an MTAP$^{high}$ CD73$^+$ tumor model where it is expected to have ADO in the tumor microenvironment but not MTA. Mice were treated with either vehicle, PEG-MTAN (50 mg/kg), anti-CTLA4 (10 mg/kg, clone UC10-4F10-11, Bio X Cell), or the combination of PEG-MTAN/anti-CTLA4. Both PEG-MTAN and anti-CTLA4 single agent arms retarded primary tumor growth and the combination was more effective, indicative of at least therapeutic additivity (FIG. 10A). As 4T1 forms pulmonary metastases, lung tissues were examined to quantify tumor colonization. All treated groups displayed significantly fewer metastatic tumor lung nodes (FIG. 10B) as compared to the vehicle control group and exemplifying the role of ADO upon metastasis.

Example 17—Efficacy of PEG-MTAN/Anti-PD1 Treatment of Murine CT26 Colon Carcinoma Allografts (MTAP$^{low}$ CD73$^+$)

Figure 11:
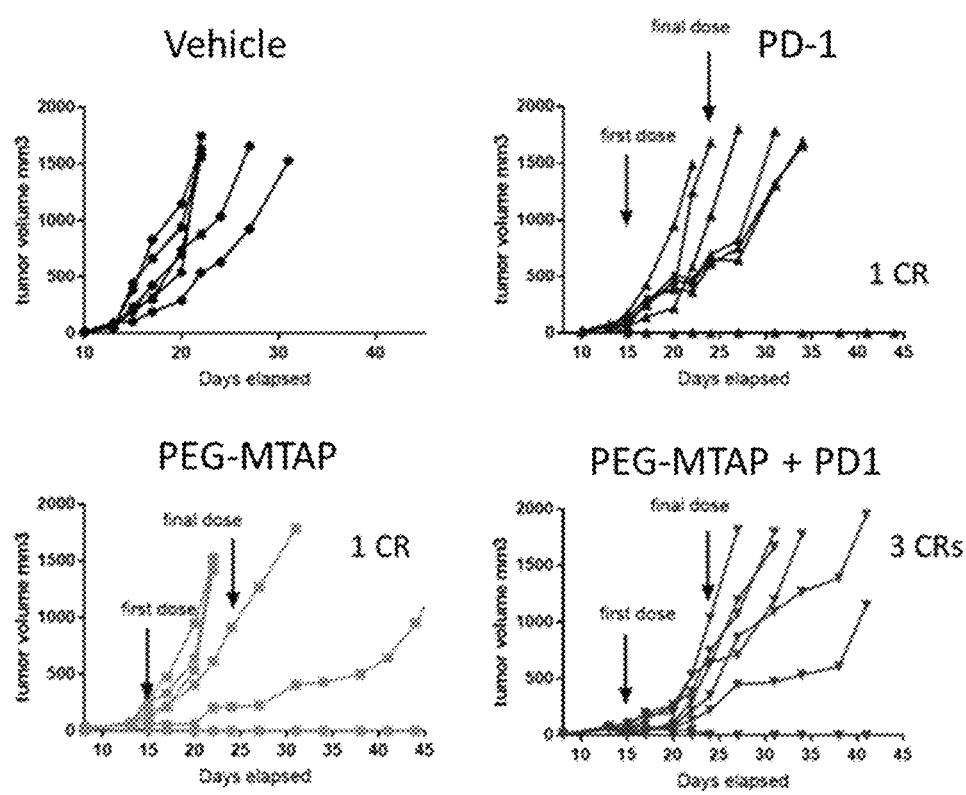
FIG. 11. Efficacy of PEG-MTAN/Anti-PD1 treatment of murine CT26 colon carcinoma allografts (MTAP$^{low}$ CD73$^+$). Tumor growth following treatment with either isotype control antibody, PEG-MTAN (50 mg/kg 3× week), anti-PD-1 (clone RMP1-14, BioXCell #BE0146, 10 mg/kg 2× week), or PEG-MTAN and anti-PD1 in combination for a total of 2 weeks.

The CT26 cell line is known to be homozygous null for CDKN2 (Castle et al., 2014), which is commonly co-deleted with MTAP; however, it was found that while MTAP is not deleted, its expression is severely impaired. Furthermore, this cell line expresses CD73 (Sun et al., 2017) and is thus expected to produce adenosine in the tumor microenvironment. To examine any potential efficacy of ADO and/or MTA depletion in an MTAP$^{low}$ CD73$^+$ tumor model as a single agent or in combination with anti-PD1 immune checkpoint inhibitor therapy, four groups of Balb/c mice bearing CT26 tumors were treated with either isotype control antibody, PEG-MTAN (50 mg/kg 3× week), anti-PD-1 (clone RMP1-14, BioXCell #BE0146, 10 mg/kg 2× week), or PEG-MTAN and anti-PD1 in combination for a total of 2 weeks. Compared to controls, both anti-PD1 and PEG-MTAN elicited heteroscedastic effects but importantly yielded a complete remission (CR) in both single agent arms. Strikingly the anti-PD1/PEG-MTAN combo showed tumor growth inhibition in the entire group and led to three complete responses (FIG. 11) suggestive of additive or synergistic efficacy.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 5,889,155
U.S. Pat. Publn. 2009/0304666
Austin-Ward and Villaseca, *Revista Medica de Chile*, 126 (7):838-845, 1998.
Ausubel et al., Current Protocols in Molecular Biology, Greene Publishing Associates and Wiley Interscience, N.Y., 1994.
Bertino et al., Targeting tumors that lack methylthioadenosine phosphorylase (MTAP) activity: current strategies. *Cancer Biology & Therapy*, 11(7): 627-632, 2011.
Bradford et al., Adenosine deaminase (ADA)-deficient severe combined immune deficiency (SCID): molecular pathogenesis and clinical manifestations. *Journal of Clinical Immunology*, 37(7): 626-637, 2017.
Bukowski et al., *Clinical Cancer Res.*, 4(10):2337-2347, 1998.

Camacho-Vanegas et al., Primate genome gain and loss: a bone dysplasia, muscular dystrophy, and bone cancer syndrome resulting from mutated retroviral-derived MTAP transcripts. *The American Journal of Human Genetics*, 90(4): 614-627, 2012.
Castle et al., Immunomic, genomic and transcriptomic characterization of CT26 colorectal carcinoma. *BMC Genomics*, 15:190, 2014.
Christodoulides et al., *Microbiology*, 144(Pt 11):3027-3037, 1998.
Davidson et al., *J. Immunother.*, 21(5):389-398, 1998.
Foye et al., Foye's Principles of Medicinal Chemistry, Lippincott Williams & Wilkins, 2007.
Gill and von Hippel, Calculation of protein extinction coefficients from amino acid sequence data. *Anal Biochem*, 182(2):319-326, 1989.
Hanibuchi et al., *Int. J. Cancer*, 78(4):480-485, 1998.
Harkki et al., *BioTechnology*, 7:596-603, 1989.
Hellstrand et al., *Acta Oncologica*, 37(4):347-353, 1998.
Henrich et al., Suppressive effects of tumor cell-derived 5'-deoxy-5'-methylthioadenosine on human T cells. *OncoImmunology*, 5(8): e1184802, 2016.
Hollander, *Front. Immun.*, 3:3, 2012.
Hopwood et al., In: *Genetic Manipulation of Streptomyces*, A Laboratory Manual, The John Innes Foundation, Norwich, Conn., 1985.
Hoover et al., The structure of human macrophage inflammatory protein-3alpha/CCL20. Linking antimicrobial and CC chemokine receptor-6-binding activities with human beta-defensins. *J Biol Chem*, 277(40):37647-37654, 2002.
Hui and Hashimoto, *Infection Immun.*, 66(11):5329-5336, 1998.
Ito et al., *J. Biochem.*, 79:1263, 1976.
Jiang et al., Comprehensive evaluation of NT5E/CD73 expression and its prognostic significance in distinct types of cancers. *BMC Cancer*, 18:267, 2018.
Kadariya et al., Mice heterozygous for germ-line mutations in methylthioadenosine phosphorylase (MTAP) die prematurely of T-cell lymphoma. *Cancer Research*, 69(14): 5961-5969, 2009.
Keyel et al., Methylthioadenosine reprograms macrophage activation through adenosine receptor stimulation. *PLoS One*, 9(8): e104210, 2014.
Kim et al., Downregulation of methylthioadenosin phosphorylase by homozygous deletion in gastric carcinoma. *Genes, Chromosomes and Cancer*, 50(6): 421-433, 2011.
Kirovski et al., Down-regulation of methylthioadenosine phosphorylase (MTAP) induces progression of hepatocellular carcinoma via accumulation of 5'-deoxy-5'-methylthioadenosine (MTA). *American Journal of Pathology*, 178(3): 1145-1152, 2011.
Lordanescu, *J. Bacteriol*, 12:597 601, 1975.
Maniatis et al., Molecular Cloning, A Laboratory Manual, Cold Spring Harbor Press, Cold Spring Harbor, N.Y., 1988.
Mellor et al., *Gene*, 24:1-14, 1983.
Morello et al., Soluble CD73 as biomarker in patients with metastatic melanoma patients treated with nivolumab. *Journal of Translational Medicine*, 15:244, 2017.
Penttila et al., *Gene*, 61:155-164, 1987.
Peters et al., A mouse model for cystinuria type I. *Hum Mol Genet* 12: 2109-2120, 2003.
Qin et al., *Proc. Natl. Acad. Sci. USA*, 95(24):14411-14416, 1998.
Remington's Pharmaceutical Sciences, 18th Ed. Mack Printing Company, 1289-1329, 1990.
Schneider et al., 671 nih image to imageJ: 25 years of image analysis. *Nature Methods*, 9:2012.
Sek et al., Targeting Adenosine Receptor Signaling in Cancer Immunotherapy. *International J. of Mol. Sciences*, 19:3837, 2018.
Sibakov et al., *Eur. J. Biochem.*, 145:567 572, 1984.
Singh et al., Picomolar transition state analogue inhibitors of human 5'-methylthioadenosine phosphorylase and X-ray structure with MT-Immucillin-A. *Biochemistry*, 43(1): 9-18, 2004.
Stevens et al., Quantification of intermediates of the methionine and polyamine metabolism by liquid chromatography-tandem mass spectrometry in cultured tumor cells and liver biopsies. *Journal of Chromatography, A* 1217 (19): 3282-3288, 2010.
Stevens et al., Quantitative analysis of 5'-deoxy-5'-methylthioadenosine in melanoma cells by liquid chromatography-stable isotope ratio tandem mass spectrometry. *Journal of Chromatography B*, 876(1): 123-128, 2008.
Stevens et al., Direct and tumor microenvironment mediated influences of 5'-deoxy-5'-(methylthio) adenosine on tumor progression of malignant melanoma. *Journal of Cellular Biochemistry*, 106(2): 210-219, 2009.
Stone et al., Strategies for optimizing the serum persistence of engineered human arginase I for cancer therapy. *Journal of Controlled Release*, 158:171-179, 2012.
Sun et al., Fasting inhibits colorectal cancer growth by reducing M2 polarization of tumor-associated macrophages. *Oncotarget*, 8:74649-74660, 2017.
Tiziani et al., Optimized metabolite extraction from blood serum for 1H nuclear magnetic resonance spectroscopy. *Analytical Biochemistry*, 377:16-23, 2008.
Tiziani et al., Metabolomics of the tumor microenvironment in pediatric acute lymphoblastic leukemia. *PLoS One*, 8:e82859, 2013.
Vandenbark et al., Inhibition of lymphocyte transformation by a naturally occurring metabolite: 5'-Methylthioadenosine. *Cellular Immunology*, 49(1): 26-33, 1980.
Vijayan et al., Targeting immunosuppressive adenosine in cancer. *Nature Reviews Cancer*, 17:709, 2017.
Ward, Proc, Embo-Alko Workshop on Molecular Biology of Filamentous Fungi, Helsinki, 119-128, 1989.
Wawrzynczak and Thorpe, In: *Immunoconjugates, Antibody Conjugates In Radioimaging And Therapy Of Cancer*, Vogel (Ed.), NY, Oxford University Press, 28, 1987.
Woollard et al., Independent Loss of Methylthioadenosine Phosphorylase (MTAP) in Primary Cutaneous T-Cell Lymphoma. *Journal of Investigative Dermatology*, 136 (6): 1238-1246, 2016.
Yu et al., Ecto-5'-nucleotidase expression is associated with the progression of renal cell carcinoma. *Oncology Letters*, 9:2485-2494, 2015.

What is claimed is:

1. A composition for treating a methylthioadenosine phosphorylase-deficient cancer comprising:
    an enzyme capable of phosphorolysis of methylthioadenosine into methylthioribose-phosphate and adenine coupled to
    a compound capable of increasing a serum half-life of the enzyme;
    wherein the enzyme comprises a sequence having at least 90% identity to SEQ ID NO: 1, and
    wherein the compound capable of increasing a serum half-life of the enzyme is a polymer that increases a hydrodynamic radius of the enzyme.

2. The composition of claim 1, wherein the compound capable of increasing a serum half-life of the enzyme is polyethylene glycol.

3. The composition of claim 2, wherein the polyethylene glycol is coupled to the enzyme via conjugation to one or more lysine residues of the enzyme.

4. A method of treating a patient having a tumor comprising administering to the patient an effective amount of a methylthioadenosine phosphorylase comprising a sequence having at least 90% identity to SEQ ID NO: 1.

5. The method of claim 4, wherein the methylthioadenosine phosphorylase is coupled to a compound capable of increasing a serum half-life of the methylthioadenosine phosphorylase.

6. The method of claim 5, wherein the methylthioadenosine phosphorylase is conjugated to polyethylene glycol.

7. The method of claim 6, further comprising administering a second anti-cancer therapy to the patient.

8. The method of claim 7, wherein the second anti-cancer therapy is an immune checkpoint inhibitor.

9. The method of claim 8, wherein the immune checkpoint inhibitor is an anti-PD1 antibody, an anti-CTLA4 antibody, or an anti-PD-L1 antibody.

10. The method of claim 5, wherein the tumor comprises:
    a deletion of a methylthioadenosine phosphorylase gene,
    an increased level of methylthioadenosine relative to a reference level, or
    a decreased level of methylthioadenosine phosphorylase relative to a reference level.

11. The method of claim 10, wherein the deletion of a methylthioadenosine phosphorylase gene comprises a homologous genetic deletion at chromosome band 9p21.

12. The method of claim 10, wherein the reference level is a level in a healthy tissue of the patient.

13. The method of claim 10, wherein the reference level is a level in a healthy individual.

14. A method of treating a patient having a tumor comprising:
    a) determining that the tumor comprises a homologous genetic deletion at chromosome 9p21 of a methylthioadenosine phosphorylase gene; and
    b) administering an enzyme capable of phosphorolysis of methylthioadenosine into methylthioribose-phosphate and adenine, wherein the enzyme comprises a sequence having at least 90% identity to SEQ ID NO: 1.

15. The method of claim 14, wherein the enzyme is conjugated to polyethylene glycol via one or more lysine residues of the enzyme.

\* \* \* \* \*

SEQUENCE LISTING

<160> NUMBER OF SEQ ID NOS: 50

<210> SEQ ID NO 1

<211> LENGTH: 283
<212> TYPE: PRT
<213> ORGANISM: Homo sapiens

<400> SEQUENCE: 1

```
Met Ala Ser Gly Thr Thr Thr Ala Val Lys Ile Gly Ile Gly
1               5                   10                  15
Gly Thr Gly Leu Asp Asp Pro Glu Ile Leu Glu Gly Arg Thr Glu Lys
                20                  25                  30
Tyr Val Asp Thr Pro Phe Gly Lys Pro Ser Asp Ala Leu Ile Leu Gly
                35                  40                  45
Lys Ile Lys Asn Val Asp Cys Val Leu Leu Ala Arg His Gly Arg Gln
50                  55                  60
His Thr Ile Met Pro Ser Lys Val Asn Tyr Gln Ala Asn Ile Trp Ala
65                  70                  75                  80
Leu Lys Glu Glu Gly Cys Thr His Val Ile Val Thr Thr Ala Cys Gly
                85                  90                  95
Ser Leu Arg Glu Glu Ile Gln Pro Gly Asp Ile Val Ile Ile Asp Gln
                100                 105                 110
Phe Ile Asp Arg Thr Thr Met Arg Pro Gln Ser Phe Tyr Asp Gly Ser
                115                 120                 125
His Ser Cys Ala Arg Gly Val Cys His Ile Pro Met Ala Glu Pro Phe
130                 135                 140
Cys Pro Lys Thr Arg Glu Val Leu Ile Glu Thr Ala Lys Lys Leu Gly
145                 150                 155                 160
Leu Arg Cys His Ser Lys Gly Thr Met Val Thr Ile Glu Gly Pro Arg
                165                 170                 175
Phe Ser Ser Arg Ala Glu Ser Phe Met Phe Arg Thr Trp Gly Ala Asp
                180                 185                 190
Val Ile Asn Met Thr Thr Val Pro Glu Val Val Leu Ala Lys Glu Ala
                195                 200                 205
Gly Ile Cys Tyr Ala Ser Ile Ala Met Ala Thr Asp Tyr Asp Cys Trp
                210                 215                 220
Lys Glu His Glu Glu Ala Val Ser Val Asp Arg Val Leu Lys Thr Leu
225                 230                 235                 240
Lys Glu Asn Ala Asn Lys Ala Lys Ser Leu Leu Leu Thr Thr Ile Pro
                245                 250                 255
Gln Ile Gly Ser Thr Glu Trp Ser Glu Thr Leu His Asn Leu Lys Asn
                260                 265                 270
Met Ala Gln Phe Ser Val Leu Leu Pro Arg His
                275                 280
```

<210> SEQ ID NO 2
<211> LENGTH: 852
<212> TYPE: DNA
<213> ORGANISM: Homo sapiens

<400> SEQUENCE: 2

```
atggcatcgg gaacaaccac gacagccgta aagattggga tcatagggggg cacaggactt    60 gatgaccctg aaattttgga aggtcgcact gagaagtacg tagacacccc attcggtaaa   120
cctagcgatg ccctgattct gggcaaaatc aaaaatgtgg attgcgtcct tcttgcccgc   180
cacggacgtc aacataccat catgccatcg aaagtcaatt atcaggcaaa tatatgggca   240
ttgaaggagg agggctgcac ccacgttatt gtgacgacag cttgtggatc gcttcgcgag   300
gagattcaac tggtgacat tgttattata gatcaattca ttgaccgcac gacaatgcgc   360
```

| | | | | | |
|---|---|---|---|---|---|
| ccgcaatcgt | tctatgacgg | ctctcacagt | tgtgcgcggg | gcgtgtgcca | catcccaatg | 420 |
| gccgagccct | tttgcccaaa | aacccgcgag | gtacttattg | agacggcgaa | aaaattggga | 480 |
| ctgcgttgtc | attccaaggg | tactatggta | actatcgagg | ggccgcgttt | tagtagccgt | 540 |
| gccgaatcgt | tcatgttccg | cacttgggga | gcggacgtca | ttaatatgac | aactgtccca | 600 |
| gaagttgttt | tagccaaaga | ggcgggaata | tgctacgcaa | gcattgctat | ggcgactgat | 660 |
| tacgactgct | ggaaagagca | cgaggaagca | gtctcagtag | atcgcgtttt | aaaaacatta | 720 |
| aaggagaacg | ctaataaggc | gaaatcccct | ttgttgacca | ctattcccca | gattggttcc | 780 |
| actgagtggt | ccgaaacctt | gcacaacctg | aagaacatgg | cccagttctc | cgtactgctt | 840 |
| ccgcgccatt | aa | | | | | 852 |

<210> SEQ ID NO 3
<211> LENGTH: 232
<212> TYPE: PRT
<213> ORGANISM: Salmonella enterica

<400> SEQUENCE: 3

Met Lys Ile Gly Ile Ile Gly Ala Met Glu Glu Glu Val Thr Leu Leu
1               5                   10                  15

Arg Asp Lys Ile Asp Asn Arg Gln Thr Ile Thr Leu Gly Gly Cys Glu
            20                  25                  30

Ile Tyr Thr Gly Gln Leu Asn Gly Thr Glu Val Ala Leu Leu Lys Ser
        35                  40                  45

Gly Ile Gly Lys Val Ala Ala Ala Leu Gly Ala Thr Leu Leu Leu Glu
    50                  55                  60

His Cys Lys Pro Asp Val Ile Asn Thr Gly Ser Ala Gly Gly Leu
65                  70                  75                  80

Ala Ser Thr Leu Lys Val Gly Asp Ile Val Val Ser Asp Glu Thr Arg
                85                  90                  95

Tyr His Asp Ala Asp Val Thr Ala Phe Gly Tyr Glu Tyr Gly Gln Leu
            100                 105                 110

Pro Gly Cys Pro Ala Gly Phe Lys Ala Asp Asp Lys Leu Ile Ala Ala
        115                 120                 125

Ala Glu Ser Cys Ile Arg Glu Leu Asn Leu Asn Ala Val Arg Gly Leu
    130                 135                 140

Ile Val Ser Gly Asp Ala Phe Ile Asn Gly Ser Val Gly Leu Ala Lys
145                 150                 155                 160

Ile Arg His Asn Phe Pro Asp Ala Val Ala Val Glu Met Glu Ala Thr
                165                 170                 175

Ala Ile Ala His Val Cys His Asn Phe Asn Val Pro Phe Val Val Val
            180                 185                 190

Arg Ala Ile Ser Asp Val Ala Asp Gln Gln Ser His Leu Ser Phe Asp
        195                 200                 205

Glu Phe Leu Ala Val Ala Ala Lys Gln Ser Thr Leu Met Val Glu Thr
    210                 215                 220

Leu Val Gln Lys Leu Ala His Gly
225                 230

<210> SEQ ID NO 4
<211> LENGTH: 699
<212> TYPE: DNA
<213> ORGANISM: Salmonella enterica

<400> SEQUENCE: 4

```
atgaaaatag gtatcatcgg agcgatggag gaggaagtca cgttgttacg cgacaagatc    60
gacaatcggc agacaataac gttagggggga tgtgaaatat acaccgggca gttaaatggg   120
acagaggtag ctttgctgaa atcaggtatt ggtaaagttg cggcagccct tggagcgact   180
cttttattgg agcattgtaa accagacgta attataaata cgggtagcgc cggaggctta   240
gcgagtacac ttaaagtcgg ggatatagtc gtgagtgacg agacacgtta ccatgatgcc   300
gacgtgactg catttggtta tgaatatggt caattgccgg ctgcccggc aggttttaag   360 gccgatgaca aacttatcgc agccgccgaa tcttgtattc gtgagctgaa cctgaatgcc   420 gtgcggggc ttatagtgtc aggcgatgcc ttcatcaatg gatcggtggg acttgccaag   480
atacgtcaca atttcccaga cgcagtcgcg gttgagatgg aggcgacggc cattgcccat   540
gtatgccata attttaacgt tccatttgtg gtcgtgcgtg cgatttctga cgtcgctgat   600
caacagagtc acctgtcgtt cgatgagttc ttggccgtgg cagctaagca atccacgctg   660
atggttgaaa cattggtcca gaaacttgcc cacgggtaa                          699
```

<210> SEQ ID NO 5
<211> LENGTH: 283
<212> TYPE: PRT
<213> ORGANISM: Macaca mulatta

<400> SEQUENCE: 5

```
Met Ala Ser Gly Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Val Arg Pro Gln Ser Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
```

```
                    245                 250                 255
Gln Ile Gly Ser Thr Glu Trp Ser Glu Thr Leu His Asn Leu Lys Asn
                260                 265                 270

Met Ala Gln Phe Ser Val Leu Leu Pro Arg His
            275                 280

<210> SEQ ID NO 6
<211> LENGTH: 283
<212> TYPE: PRT
<213> ORGANISM: Callithrix jacchus

<400> SEQUENCE: 6

Met Ala Ser Ser Thr Thr Thr Thr Val Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Met Arg Pro Gln Ser Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Leu Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Met Glu Trp Ser Glu Thr Leu His Ser Leu Lys Asn
            260                 265                 270

Met Ala Gln Phe Ser Val Leu Leu Pro Arg His
        275                 280

<210> SEQ ID NO 7
<211> LENGTH: 283
<212> TYPE: PRT
<213> ORGANISM: Saimiri boliviensis

<400> SEQUENCE: 7

Met Ala Ser Ser Thr Thr Thr Thr Val Val Lys Ile Gly Ile Ile Gly
```

```
                1               5                  10                 15
            Gly Thr Gly Leu Asp Asp Pro Glu Ile Leu Glu Gly Arg Thr Glu Lys
                        20                  25                 30

Tyr Val Asp Thr Pro Phe Gly Lys Pro Ser Asp Ala Leu Ile Leu Gly
                        35                  40                 45

Lys Ile Lys Asn Val Asp Cys Val Leu Leu Ala Arg His Gly Arg Gln
                        50                  55                 60

His Thr Ile Met Pro Ser Lys Val Asn Tyr Gln Ala Asn Ile Trp Ala
            65                  70                  75                 80

Leu Lys Glu Glu Gly Cys Thr His Val Ile Val Thr Thr Ala Cys Gly
                        85                  90                 95

Ser Leu Arg Glu Glu Ile Gln Pro Gly Asp Ile Val Ile Ile Asp Gln
                        100                 105                110

Phe Ile Asp Arg Thr Thr Val Arg Pro Gln Ser Phe Tyr Asp Gly Ser
                        115                 120                125

His Ser Cys Ala Arg Gly Val Cys His Ile Pro Met Ala Glu Pro Phe
                        130                 135                140

Cys Pro Lys Thr Arg Glu Val Leu Ile Glu Thr Ala Lys Lys Leu Gly
            145                 150                 155                160

Leu Arg Cys His Ser Lys Gly Thr Met Val Thr Ile Glu Gly Pro Arg
                        165                 170                175

Phe Ser Ser Arg Ala Glu Ser Phe Met Phe Arg Thr Trp Gly Ala Asp
                        180                 185                190

Val Ile Asn Met Thr Thr Val Pro Glu Val Val Leu Ala Lys Glu Ala
                        195                 200                205

Gly Ile Cys Tyr Ala Ser Ile Ala Met Ala Thr Asp Tyr Asp Cys Trp
                        210                 215                220

Lys Glu His Glu Glu Ala Val Ser Val Asp Arg Val Leu Lys Thr Leu
            225                 230                 235                240

Lys Glu Asn Ala Asn Lys Ala Lys Ser Leu Leu Thr Thr Ile Pro
                        245                 250                255

Gln Ile Gly Ser Met Glu Trp Ser Glu Thr Leu His Ser Leu Lys Asn
                        260                 265                270

Met Ala Gln Phe Ser Val Leu Leu Pro Arg His
                        275                 280

<210> SEQ ID NO 8
<211> LENGTH: 283
<212> TYPE: PRT
<213> ORGANISM: Aotus nancymaae

<400> SEQUENCE: 8

Met Ala Ser Ser Thr Thr Thr Val Val Lys Ile Gly Ile Gly
            1               5                  10                 15

Gly Thr Gly Leu Asp Asp Pro Glu Ile Leu Glu Gly Arg Thr Glu Lys
                        20                  25                 30

Tyr Val Asp Thr Pro Phe Gly Lys Pro Ser Asp Ala Leu Ile Leu Gly
                        35                  40                 45

Lys Ile Lys Asn Val Asp Cys Val Leu Leu Ala Arg His Gly Arg Gln
                        50                  55                 60

His Thr Ile Met Pro Ser Lys Val Asn Tyr Gln Ala Asn Ile Trp Ala
            65                  70                  75                 80

Leu Lys Glu Glu Gly Cys Thr His Val Ile Val Thr Thr Ala Cys Gly
                        85                  90                 95
```

```
Ser Leu Arg Glu Glu Ile Gln Pro Gly Asp Ile Val Ile Asp Gln
            100                 105                 110

Phe Ile Asp Arg Thr Thr Met Arg Pro Gln Ser Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Tyr Met Leu Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Ser Leu Lys Asn
            260                 265                 270

Met Ala Gln Phe Ser Val Leu Leu Pro Arg His
            275                 280

<210> SEQ ID NO 9
<211> LENGTH: 283
<212> TYPE: PRT
<213> ORGANISM: Camelus dromedarius

<400> SEQUENCE: 9

Met Ala Ser Gly Ala Thr Pro Ala Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Ile Arg Pro Gln Ser Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Ile Thr Ile Glu Gly Pro Arg
                165                 170                 175

Phe Ser Ser Arg Ala Glu Ser Phe Met Phe Arg Thr Trp Gly Ala Asp
            180                 185                 190
```

```
Val Ile Asn Met Thr Thr Val Pro Glu Val Val Leu Ala Lys Glu Ala
            195                 200                 205

Gly Met Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Ser Thr Ile Pro
                245                 250                 255

Gln Ile Gly Ser Val Glu Trp Ser Glu Thr Leu His Asn Leu Lys Asn
            260                 265                 270

Met Ala Gln Phe Ser Val Leu Leu Pro Arg His
            275                 280

<210> SEQ ID NO 10
<211> LENGTH: 283
<212> TYPE: PRT
<213> ORGANISM: Ochotona princeps

<400> SEQUENCE: 10

Met Ala Ser Gly Ala Ala Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Leu Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Thr Arg Pro Gln Thr Phe Tyr Asp Gly Ser
        115                 120                 125

His Ser Cys Ala Arg Gly Val Cys His Ile Pro Met Val Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Ile Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Ala Ile Pro
                245                 250                 255

Gln Ile Gly Ser Thr Glu Trp Ser Glu Thr Leu His Asn Leu Lys Asn
            260                 265                 270

Met Ala Gln Phe Ser Val Leu Leu Pro Arg His
```

-continued

```
                275                 280

<210> SEQ ID NO 11
<211> LENGTH: 284
<212> TYPE: PRT
<213> ORGANISM: Oryctolagus cuniculus

<400> SEQUENCE: 11

Met Ala Ser Gly Ala Thr Thr Ala Ala Val Lys Ile Gly Ile Ile
1               5                   10                  15

Gly Gly Thr Gly Leu Asp Asp Pro Glu Ile Leu Glu Gly Arg Thr Glu
                20                  25                  30

Lys Tyr Val Asp Thr Pro Phe Gly Lys Pro Ser Asp Ala Leu Ile Leu
            35                  40                  45

Gly Lys Ile Lys Asn Val Asp Cys Val Leu Leu Ala Arg His Gly Arg
        50                  55                  60

Gln His Thr Ile Met Pro Ser Lys Val Asn Tyr Gln Ala Asn Ile Trp
65                  70                  75                  80

Ala Leu Lys Glu Glu Gly Cys Thr His Val Ile Val Thr Thr Ala Cys
                85                  90                  95

Gly Ser Leu Arg Glu Glu Ile Gln Pro Gly Asp Ile Val Ile Ile Asp
            100                 105                 110

Gln Phe Ile Asp Arg Thr Met Thr Arg Pro Gln Thr Phe Tyr Asp Gly
        115                 120                 125

Ser His Ser Cys Ala Arg Gly Val Cys His Ile Pro Met Ala Glu Pro
    130                 135                 140

Phe Cys Pro Lys Thr Arg Glu Val Leu Ile Glu Thr Ala Lys Lys Leu
145                 150                 155                 160

Gly Leu Arg Cys His Ser Lys Gly Thr Met Val Thr Ile Glu Gly Pro
                165                 170                 175

Arg Phe Ser Ser Arg Ala Glu Ser Phe Met Phe Arg Thr Trp Gly Ala
            180                 185                 190

Asp Val Ile Asn Met Thr Thr Val Pro Glu Val Val Leu Ala Lys Glu
        195                 200                 205

Ala Gly Ile Cys Tyr Ala Ser Ile Ala Met Ala Thr Asp Tyr Asp Cys
    210                 215                 220

Trp Lys Glu His Glu Glu Ala Val Ser Val Asp Arg Val Leu Lys Thr
225                 230                 235                 240

Leu Lys Glu Asn Ala Asn Lys Ala Lys Ser Leu Leu Leu Thr Thr Ile
                245                 250                 255

Pro Gln Ile Gly Ser Thr Glu Trp Ser Glu Thr Leu His Asn Leu Lys
            260                 265                 270

Asn Met Ala Gln Phe Ser Val Leu Leu Pro Arg His
        275                 280

<210> SEQ ID NO 12
<211> LENGTH: 283
<212> TYPE: PRT
<213> ORGANISM: Mustela putorius

<400> SEQUENCE: 12

Met Ala Ser Gly Ala Thr Pro Thr Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
```

```
            35                  40                  45
Lys Ile Lys Asn Val Asp Cys Val Leu Leu Ala Arg His Gly Arg Gln
 50                  55                  60

His Thr Ile Met Pro Ser Lys Val Asn Tyr Gln Ala Asn Ile Trp Ala
 65                  70                  75                  80

Leu Lys Glu Glu Gly Cys Thr His Ile Val Thr Thr Ala Cys Gly
                 85                  90                  95

Ser Leu Arg Glu Glu Ile Gln Pro Gly Asp Ile Val Ile Ile Asp Gln
                100                 105                 110

Phe Ile Asp Arg Thr Thr Lys Arg Pro Gln Thr Phe Tyr Asp Gly Ser
            115                 120                 125

His Ser Cys Thr Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
                260                 265                 270

Met Ala Gln Phe Ser Val Leu Leu Pro Arg His
            275                 280

<210> SEQ ID NO 13
<211> LENGTH: 283
<212> TYPE: PRT
<213> ORGANISM: Ailuropoda melanoleuca

<400> SEQUENCE: 13

Met Ala Ser Gly Ala Thr Pro Thr Ala Val Lys Ile Gly Ile Ile Gly
 1               5                  10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
 50                  55                  60

His Thr Ile Met Pro Ser Lys Val Asn Tyr Gln Ala Asn Ile Trp Ala
 65                  70                  75                  80

Leu Lys Glu Glu Gly Cys Thr His Ile Val Thr Thr Ala Cys Gly
                 85                  90                  95

Ser Leu Arg Glu Glu Ile Gln Pro Gly Asp Ile Val Ile Ile Asp Gln
                100                 105                 110

Phe Ile Asp Arg Thr Thr Lys Arg Pro Gln Thr Phe Tyr Asp Gly Ser
            115                 120                 125
```

-continued

```
His Ser Cys Ala Arg Gly Val Cys His Ile Pro Met Ala Glu Pro Phe
    130                 135                 140

Cys Pro Lys Thr Arg Glu Val Leu Thr Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Ala Ile Pro
                245                 250                 255

Gln Ile Gly Ser Met Glu Trp Ser Glu Thr Leu His Asn Leu Lys Asn
                260                 265                 270

Met Ala Gln Phe Ser Val Leu Leu Pro Arg His
            275                 280

<210> SEQ ID NO 14
<211> LENGTH: 283
<212> TYPE: PRT
<213> ORGANISM: Galeopterus variegatus

<400> SEQUENCE: 14

Met Ala Ser Gly Ala Ala Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Asp Glu Ile Gln Pro Gly Asp Ile Val Ile Ile Asp Gln
            100                 105                 110

Phe Ile Asp Arg Thr Thr Lys Arg Pro Gln Ser Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Met Glu Ser Phe Leu Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
    210                 215                 220
```

```
Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
            245                 250                 255

Gln Ile Gly Ser Met Glu Trp Ser Glu Thr Leu His Asn Leu Lys Asn
        260                 265                 270

Met Ala Gln Phe Ser Ile Leu Val Pro Arg His
    275                 280
```

<210> SEQ ID NO 15
<211> LENGTH: 344
<212> TYPE: PRT
<213> ORGANISM: Camelus ferus

<400> SEQUENCE: 15

```
Met Pro Gln Ala Thr Pro Met Glu Pro Gly Ser Gln Gln Ala Pro Ala
1               5                   10                  15

Asn Ser Asp Phe Gln Leu Thr Met Lys Phe Asn Glu Ser Arg Ala Ala
            20                  25                  30

Arg Val Asn Pro Leu Arg Ala Ser Pro Arg Val Val Ala Ala Pro
        35                  40                  45

Ser Gln Arg Arg His Gly Leu Arg Cys His Ser Arg Gly Arg Asp Ser
    50                  55                  60

Gly Ala Thr Pro Ala Ala Val Lys Ile Gly Ile Gly Gly Thr Gly
65                  70                  75                  80

Leu Asp Asp Pro Glu Ile Leu Glu Gly Arg Thr Glu Lys Tyr Val Asp
                85                  90                  95

Thr Pro Phe Gly Lys Pro Ser Asp Ala Leu Ile Leu Gly Lys Ile Lys
            100                 105                 110

Asn Val Asp Cys Val Leu Leu Ala Arg His Gly Arg Gln His Thr Ile
        115                 120                 125

Met Pro Ser Lys Val Asn Tyr Gln Ala Asn Ile Trp Ala Leu Lys Glu
    130                 135                 140

Glu Gly Cys Thr His Val Ile Val Thr Thr Ala Cys Gly Ser Leu Arg
145                 150                 155                 160

Glu Glu Ile Gln Pro Gly Asp Ile Val Ile Asp Gln Phe Ile Asp
                165                 170                 175

Arg Thr Thr Ile Arg Pro Gln Ser Phe Tyr Asp Gly Ser His Ser Cys
            180                 185                 190

Ala Arg Gly Val Cys His Ile Pro Met Ala Glu Pro Phe Cys Pro Lys
        195                 200                 205

Thr Arg Glu Val Leu Ile Glu Thr Ala Lys Lys Leu Gly Leu Arg Cys
    210                 215                 220

His Ser Lys Gly Thr Met Val Thr Ile Lys Gly Pro Arg Phe Ser Ser
225                 230                 235                 240

Arg Ala Glu Ser Phe Met Phe Arg Thr Trp Gly Ala Asp Val Ile Asn
                245                 250                 255

Met Thr Thr Val Pro Glu Val Val Leu Ala Lys Glu Ala Gly Met Cys
            260                 265                 270

Tyr Ala Ser Ile Ala Met Ala Thr Asp Tyr Asp Cys Trp Lys Glu His
        275                 280                 285

Glu Glu Ala Val Ser Val Asp Arg Val Leu Lys Thr Leu Lys Glu Asn
    290                 295                 300

Ala Asn Lys Ala Lys Ser Leu Leu Leu Ser Thr Ile Pro Gln Ile Gly
```

-continued

```
                305                 310                 315                 320
Ser Val Glu Trp Ser Glu Thr Leu His Asn Leu Lys Asn Met Ala Gln
                    325                 330                 335

Phe Ser Val Leu Leu Pro Arg His
                340

<210> SEQ ID NO 16
<211> LENGTH: 283
<212> TYPE: PRT
<213> ORGANISM: Hipposideros armiger

<400> SEQUENCE: 16

Met Ala Ser Cys Ala Thr Pro Thr Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
                35                  40                  45

Lys Ile Lys Asn Val Asp Cys Val Leu Leu Ala Arg His Gly Arg Gln
            50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
                100                 105                 110

Phe Ile Asp Arg Thr Thr Thr Arg Pro Gln Thr Phe Tyr Asp Gly Ser
                115                 120                 125

His Ser Cys Ala Arg Gly Val Cys His Ile Pro Met Ala Glu Pro Phe
            130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Leu Thr Ile Glu Gly Pro Arg
                165                 170                 175

Phe Ser Ser Arg Ala Glu Ser Phe Met Phe Arg Thr Trp Gly Ala Asp
                180                 185                 190

Val Ile Asn Met Thr Thr Ile Pro Glu Val Val Leu Ala Lys Glu Ala
                195                 200                 205

Gly Leu Cys Tyr Ala Ser Ile Ala Met Ala Thr Asp Tyr Asp Cys Trp
            210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Val Gly Ser Met Glu Trp Ser Glu Thr Leu His Asn Leu Lys Asn
                260                 265                 270

Met Ala Gln Phe Ser Val Leu Leu Pro Arg His
                275                 280

<210> SEQ ID NO 17
<211> LENGTH: 283
<212> TYPE: PRT
<213> ORGANISM: Felis catus

<400> SEQUENCE: 17

Met Ala Ser Gly Ala Thr Pro Ala Ala Val Lys Ile Gly Ile Ile Gly
```

```
            1               5                  10                 15
        Gly Thr Gly Leu Asp Asp Pro Glu Ile Leu Glu Gly Arg Thr Glu Lys
                        20                 25                 30

Tyr Val Asp Thr Pro Phe Gly Lys Pro Ser Asp Ala Leu Ile Leu Gly
                        35                 40                 45

Lys Ile Lys Asn Val Asp Cys Val Leu Leu Ala Arg His Gly Arg Gln
                        50                 55                 60

His Ser Ile Met Pro Ser Lys Val Asn Tyr Gln Ala Asn Ile Trp Ala
        65                      70                 75                 80

Leu Lys Glu Glu Gly Cys Thr His Val Ile Val Thr Thr Ala Cys Gly
                        85                 90                 95

Ser Leu Arg Glu Glu Ile Gln Pro Gly Asp Ile Val Ile Ile Asp Gln
                        100                105                110

Phe Ile Asp Arg Thr Thr Ile Arg Pro Gln Thr Phe Tyr Asp Gly Ser
                        115                120                125

His Ser Cys Ala Arg Gly Val Cys His Ile Pro Met Ala Glu Pro Phe
                        130                135                140

Cys Pro Lys Thr Arg Glu Val Leu Ile Glu Thr Ala Lys Lys Leu Gly
        145                     150                155                160

Leu Arg Cys His Ser Lys Gly Thr Met Val Thr Ile Glu Gly Pro Arg
                        165                170                175

Phe Ser Ser Arg Ala Glu Ser Phe Met Phe Arg Thr Trp Gly Ala Asp
                        180                185                190

Val Ile Asn Met Thr Thr Val Pro Glu Val Val Leu Ala Lys Glu Ala
                        195                200                205

Gly Ile Cys Tyr Ala Ser Ile Ala Met Ala Thr Asp Tyr Asp Cys Trp
                        210                215                220

Lys Glu His Glu Glu Ala Val Ser Val Asp Arg Val Leu Lys Thr Leu
        225                     230                235                240

Lys Glu Asn Ala Asn Lys Ala Lys Ser Leu Leu Thr Thr Ile Pro
                        245                250                255

Gln Ile Gly Ser Met Glu Trp Ser Glu Thr Leu Gln Asn Leu Lys Asn
                        260                265                270

Thr Ala Gln Phe Ser Val Leu Leu Pro Arg His
                        275                280

<210> SEQ ID NO 18
<211> LENGTH: 283
<212> TYPE: PRT
<213> ORGANISM: Odobenus rosmarus

<400> SEQUENCE: 18

Met Ala Ser Gly Ala Ile Pro Thr Ala Val Lys Ile Gly Ile Ile Gly
        1               5                  10                 15

Gly Thr Gly Leu Asp Asp Pro Glu Ile Leu Glu Gly Arg Thr Glu Lys
                        20                 25                 30

Tyr Val Asp Thr Pro Phe Gly Lys Pro Ser Asp Ala Leu Ile Leu Gly
                        35                 40                 45

Lys Ile Lys Asn Val Asp Cys Val Leu Leu Ala Arg His Gly Arg Gln
                        50                 55                 60

His Thr Ile Met Pro Ser Lys Val Asn Tyr Gln Ala Asn Ile Trp Ala
        65                      70                 75                 80

Leu Lys Glu Glu Gly Cys Thr His Val Ile Val Thr Thr Ala Cys Gly
                        85                 90                 95
```

```
Ser Leu Arg Glu Glu Ile Gln Pro Gly Asp Ile Val Ile Asp Gln
            100                 105                 110

Phe Ile Asp Arg Thr Thr Lys Arg Pro Gln Thr Phe Tyr Asp Gly Ser
            115                 120                 125

His Ser Ser Thr Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
        260                 265                 270

Met Ala Gln Phe Ser Val Leu Leu Pro Arg His
            275                 280
```

<210> SEQ ID NO 19
<211> LENGTH: 283
<212> TYPE: PRT
<213> ORGANISM: Ictidomys tridecemlineatus

<400> SEQUENCE: 19

```
Met Ala Ser Gly Ala Ala Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
        50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Asp Gln
            100                 105                 110

Phe Ile Asp Arg Thr Thr Met Arg Pro Gln Thr Phe Tyr Asp Gly Cys
            115                 120                 125

His Ser Cys Thr Arg Gly Val Cys His Ile Pro Leu Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Ile Val Thr Ile Glu Gly Pro Arg
                165                 170                 175

Phe Ser Ser Arg Ala Glu Ser Phe Met Phe Arg Thr Trp Gly Ala Asp
            180                 185                 190
```

```
Val Ile Asn Met Thr Thr Val Pro Glu Val Val Leu Ala Lys Glu Ala
            195                 200                 205

Gly Ile Cys Tyr Ala Gly Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ala Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
            275                 280
```

<210> SEQ ID NO 20
<211> LENGTH: 283
<212> TYPE: PRT
<213> ORGANISM: Leptonychotes weddelli

<400> SEQUENCE: 20

```
Met Ala Ser Gly Ala Thr Pro Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Ile Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Lys Arg Pro Gln Thr Phe Tyr Asp Gly Ser
        115                 120                 125

His Ser Ser Thr Arg Gly Val Cys His Ile Pro Val Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Val Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
```

<210> SEQ ID NO 21
<211> LENGTH: 283
<212> TYPE: PRT
<213> ORGANISM: Rhinolophus sinicus

<400> SEQUENCE: 21

Met Ala Ser Gly Ala Thr Pro Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Thr Arg Pro Gln Thr Phe Tyr Asp Gly Ser
        115                 120                 125

Arg Ser Cys Ser Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Leu Thr Ile Glu Gly Pro Arg
                165                 170                 175

Phe Ser Ser Arg Ser Glu Ser Ile Met Phe Arg Thr Trp Gly Ala Asp
            180                 185                 190

Val Ile Asn Met Thr Thr Ile Pro Glu Val Val Leu Ala Lys Glu Ala
        195                 200                 205

Gly Leu Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
        275                 280

<210> SEQ ID NO 22
<211> LENGTH: 283
<212> TYPE: PRT
<213> ORGANISM: Castor canadensis

<400> SEQUENCE: 22

Met Ala Leu Ser Ala Ala Gly Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly

```
                35                  40                  45
Lys Ile Lys Asn Val Asp Cys Val Leu Leu Ala Arg His Gly Arg Gln
             50                  55                  60

His Thr Ile Met Pro Ser Lys Val Asn Tyr Gln Ala Asn Ile Trp Ala
 65                  70                  75                  80

Leu Lys Glu Glu Gly Cys Thr His Val Ile Val Thr Thr Ala Cys Gly
                 85                  90                  95

Ser Leu Arg Glu Glu Ile Gln Pro Gly Asp Ile Val Ile Ile Asp Gln
            100                 105                 110

Phe Ile Asp Arg Thr Ser Ile Arg Pro Gln Thr Phe Tyr Asp Gly Ser
        115                 120                 125

His Ser Cys Ser Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Val Val Thr Ile Glu Gly Pro Arg
                165                 170                 175

Phe Ser Ser Arg Ala Glu Ser Phe Met Phe Arg Thr Trp Gly Ala Asp
            180                 185                 190

Ile Ile Asn Met Thr Thr Val Pro Glu Val Ile Leu Ala Lys Glu Ala
        195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
        275                 280

<210> SEQ ID NO 23
<211> LENGTH: 283
<212> TYPE: PRT
<213> ORGANISM: Chrysochloris asiatica

<400> SEQUENCE: 23

Met Ala Ser Gly Ala Ala Thr Thr Ala Val Lys Ile Gly Ile Ile Gly
 1               5                  10                  15

Gly Thr Gly Leu Asp Asp Pro Asp Ile Leu Glu Gly Arg Thr Glu Lys
                20                  25                  30

Tyr Val Asp Thr Pro Phe Gly Lys Pro Ser Asp Ala Leu Ile Leu Gly
             35                  40                  45

Lys Ile Lys Asn Val Asp Cys Val Leu Leu Ala Arg His Gly Arg Gln
         50                  55                  60

His Thr Ile Met Pro Ser Lys Val Asn Tyr Gln Ala Asn Ile Trp Ala
 65                  70                  75                  80

Leu Lys Glu Gln Gly Cys Thr His Ile Ile Val Thr Thr Ala Cys Gly
                 85                  90                  95

Ser Leu Arg Glu Glu Ile Gln Pro Gly Asp Ile Ile Leu Ile Asp Gln
            100                 105                 110

Phe Ile Asp Arg Thr Ser Ile Arg Pro Gln Thr Phe Tyr Asp Gly Ser
        115                 120                 125
```

```
Arg Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Ile Thr Ile Glu Gly Pro Arg
                165                 170                 175

Phe Ser Ser Arg Ala Glu Ser Phe Met Phe Arg Thr Trp Gly Ala Asp
                180                 185                 190

Val Ile Asn Met Thr Thr Val Pro Glu Val Val Leu Ala Lys Glu Ala
                195                 200                 205

Gly Ile Cys Tyr Ala Ser Ile Ala Met Ala Thr Asp Tyr Asp Cys Trp
    210                 215                 220

Lys Glu His Glu Glu Ala Val Ser Val Asp Lys Val Leu Lys Asn Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
                260                 265                 270

Met Ala Gln Phe Ser Val Leu Val Pro Arg His
    275                 280
```

<210> SEQ ID NO 24
<211> LENGTH: 283
<212> TYPE: PRT
<213> ORGANISM: Myotis lucifugus

<400> SEQUENCE: 24

```
Met Ala Ser Gly Ala Thr Leu Pro Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
                100                 105                 110

Phe Ile Asp Arg Thr Thr Met Arg Pro Gln Thr Phe Tyr Asp Gly Ser
            115                 120                 125

His Ser Cys Ala Arg Gly Val Cys His Ile Pro Met Ala Glu Pro Phe
    130                 135                 140

Cys Pro Lys Thr Arg Glu Val Leu Thr Glu Thr Ala Lys Lys Leu Gly
145                 150                 155                 160

Leu Arg Tyr His Ser Lys Gly Thr Met Leu Thr Ile Glu Gly Pro Arg
                165                 170                 175

Phe Ser Ser Arg Ala Glu Ser Ile Met Phe Arg Thr Trp Gly Ala Asp
                180                 185                 190

Val Ile Asn Met Thr Thr Val Pro Glu Val Val Leu Ala Lys Glu Ala
                195                 200                 205

Gly Leu Cys Tyr Ala Ser Ile Ala Met Ala Thr Asp Tyr Asp Cys Trp
    210                 215                 220
```

```
Lys Glu His Glu Glu Val Val Ser Val Asp Arg Val Leu Lys Thr Leu
225                 230                 235                 240

Lys Glu Asn Ala Asn Lys Ala Lys Ser Leu Leu Thr Thr Ile Pro
            245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
        275                 280

<210> SEQ ID NO 25
<211> LENGTH: 283
<212> TYPE: PRT
<213> ORGANISM: Pteropus alecto

<400> SEQUENCE: 25

Met Val Pro Gly Ala Ser Pro Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Thr Arg Pro Gln Thr Phe Tyr Asp Gly Ser
        115                 120                 125

His Pro Cys Ala Arg Gly Val Cys His Ile Pro Met Ala Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Leu Thr Ile Glu Gly Pro Arg
                165                 170                 175

Phe Ser Ser Arg Ala Glu Ser Phe Met Phe Arg Gly Trp Gly Ala Asp
            180                 185                 190

Val Ile Asn Met Thr Thr Val Pro Glu Val Val Leu Ala Lys Glu Ala
        195                 200                 205

Gly Leu Cys Tyr Ala Ser Ile Ala Met Ala Thr Asp Tyr Asp Cys Trp
210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
            245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
        275                 280

<210> SEQ ID NO 26
<211> LENGTH: 283
<212> TYPE: PRT
```

<213> ORGANISM: Tupaia chinensis

<400> SEQUENCE: 26

Met Ala Ser Gly Ala Ala Asn Asn Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Ile Arg Pro Gln Thr Phe Tyr Asp Gly Ser
        115                 120                 125

His Pro Cys Ala Arg Gly Val Cys His Ile Pro Val Ala Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Leu Ile Gly Ser Met Glu Trp Ser Glu Thr Leu His Asn Leu Lys Asn
            260                 265                 270

Thr Ala Gln Phe Ser Val Leu Leu Pro Arg His
        275                 280

<210> SEQ ID NO 27
<211> LENGTH: 283
<212> TYPE: PRT
<213> ORGANISM: Loxodonta africana

<400> SEQUENCE: 27

Met Ala Ser Ser Ala Ala Thr Thr Thr Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala

```
              65                  70                  75                  80
Leu Lys Glu Glu Gly Cys Thr His Ile Ile Val Thr Thr Ala Cys Gly
                    85                  90                  95

Ser Leu Arg Glu Glu Val Gln Pro Gly Asp Ile Val Ile Asp Gln
                100                 105                 110

Phe Ile Asp Arg Thr Thr Thr Arg Pro Gln Thr Phe Tyr Asp Gly Ser
                115                 120                 125

Arg Ser Cys Ala Arg Gly Val Cys His Ile Pro Met Ala Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Ile Thr Ile Glu Gly Pro Arg
                165                 170                 175

Phe Ser Ser Arg Ala Glu Ser Leu Met Phe Arg Thr Trp Gly Ala Asp
                180                 185                 190

Val Ile Asn Met Thr Thr Val Pro Glu Val Val Leu Ala Lys Glu Ala
                195                 200                 205

Gly Ile Cys Tyr Ala Ser Ile Ala Met Ala Thr Asp Tyr Asp Cys Trp
210                 215                 220

Lys Glu His Glu Glu Ala Val Ser Val Asp Arg Val Leu Lys Thr Leu
225                 230                 235                 240

Lys Glu Asn Ala Asn Lys Ala Thr Ser Val Leu Leu Thr Thr Ile Pro
                245                 250                 255

Gln Ile Gly Ser Met Glu Trp Ser Glu Thr Leu His Asn Leu Lys Asn
                260                 265                 270

Met Ala Gln Phe Ser Val Leu Leu Pro Arg His
                275                 280

<210> SEQ ID NO 28
<211> LENGTH: 283
<212> TYPE: PRT
<213> ORGANISM: Erinaceus europaeus

<400> SEQUENCE: 28

Met Ala Ser Gly Ala Ala Ala Thr Pro Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
                35                  40                  45

Lys Ile Lys Asn Val Asp Cys Val Leu Leu Ala Arg His Gly Arg Gln
            50                  55                  60

His Thr Ile Met Pro Ser Arg Val Asn Tyr Gln Ala Asn Ile Trp Ala
65                  70                  75                  80

Leu Lys Glu Glu Gly Cys Thr His Ile Ile Val Thr Thr Ala Cys Gly
                    85                  90                  95

Ser Leu Arg Glu Glu Ile Gln Pro Gly Asp Ile Val Ile Asp Gln
                100                 105                 110

Phe Ile Asp Arg Thr Thr Lys Arg Ala Gln Thr Phe Tyr Asp Gly Ser
                115                 120                 125

His Ser Cys Ala Arg Gly Val Cys His Ile Pro Val Ala Glu Pro Phe
130                 135                 140

Cys Pro Lys Thr Arg Glu Val Leu Ile Glu Thr Ala Lys Lys Leu Gly
145                 150                 155                 160
```

Leu Arg Cys His Ser Lys Gly Thr Met Val Thr Ile Glu Gly Pro Arg
            165                 170                 175

Phe Ser Ser Arg Ala Glu Ser Phe Met Phe Arg Thr Trp Gly Ala Asp
        180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
            245                 250                 255

Gln Ile Gly Ser Met Glu Trp Ser Glu Thr Leu His Asn Leu Lys Asn
            260                 265                 270

Met Ala His Phe Ser Val Leu Leu Pro Arg His
            275                 280

<210> SEQ ID NO 29
<211> LENGTH: 280
<212> TYPE: PRT
<213> ORGANISM: Mandrillus leucophaeus

<400> SEQUENCE: 29

Met Ala Ser Gly Thr Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
            85                  90                  95

Ser Leu Arg Glu Glu Ile Gln Pro Gly Asp Ile Val Ile Ile Asp Gln
            100                 105                 110

Phe Ile Asp Arg Thr Thr Met Arg Pro Gln Ser Phe Tyr Asp Gly Ser
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
            165                 170                 175

Phe Ser Ser Arg Ala Glu Ser Phe Met Phe Arg Thr Trp Gly Ala Asp
        180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
            245                 250                 255

Gln Ile Gly Ser Thr Glu Trp Ser Glu Thr Leu His Asn Leu Lys Val
            260                 265                 270

Arg Ser Ala Phe Tyr Leu Leu Pro
            275                 280

<210> SEQ ID NO 30
<211> LENGTH: 283
<212> TYPE: PRT
<213> ORGANISM: Eptesicus fuscus

<400> SEQUENCE: 30

Met Ala Ser Gly Ala Thr Pro Thr Ala Val Lys Ile Gly Ile Val Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Ala Met Arg Pro Gln Thr Phe Tyr Asp Gly Asn
        115                 120                 125

His Ser Cys Ala Arg Gly Val Cys His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Tyr His Ser Lys Gly Thr Val Leu Thr Ile Glu Gly Pro Arg
                165                 170                 175

Phe Ser Ser Arg Ala Glu Ser Ile Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Leu Cys Tyr Ala Ser Ile Ala Met Ala Thr Asp Tyr Asp Cys Trp
    210                 215                 220

Lys Glu His Glu Glu Val Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
            275                 280

<210> SEQ ID NO 31
<211> LENGTH: 283
<212> TYPE: PRT
<213> ORGANISM: Propithecus coquereli

<400> SEQUENCE: 31

Met Ala Ser Ser Ala Ala Thr Ala Ala Val Lys Ile Gly Ile Ile Gly
1               5                   10                  15

-continued

```
Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
 50                  55                  60

His Thr Ile Val Pro Ser Lys Ile Asn Tyr Gln Ala Asn Ile Trp Ala
 65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Met Ile Ile Ile Asp Gln
            100                 105                 110

Phe Ile Asp Arg Thr Thr Met Arg Pro Gln Thr Phe Tyr Asp Gly Ser
        115                 120                 125

His Ser Cys Ala Arg Gly Val Cys His Ile Pro Val Ala Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Ala Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Ile Ala Thr Asp Tyr Asp Cys Trp
    210                 215                 220

Lys Glu His Glu Glu Glu Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
            260                 265                 270

Val Ala Gln Phe Ser Val Leu Leu Pro Arg His
        275                 280

<210> SEQ ID NO 32
<211> LENGTH: 334
<212> TYPE: PRT
<213> ORGANISM: Pan troglodytes

<400> SEQUENCE: 32

Met Ala Ser Gly Thr Thr Thr Thr Ala Val Lys Ile Gly Ile Ile Gly
  1               5                  10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
 50                  55                  60

His Thr Ile Met Pro Ser Lys Val Asn Tyr Gln Ala Asn Ile Trp Ala
 65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
```

```
            100                 105                 110
Phe Ile Asp Arg Thr Thr Met Arg Pro Gln Ser Phe Tyr Asp Gly Ser
            115                 120                 125

His Ser Cys Ala Arg Gly Val Cys His Ile Pro Met Ala Glu Pro Phe
            130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                    165                 170                 175

Phe Ser Ser Arg Ala Glu Ser Phe Met Phe Arg Thr Trp Gly Ala Asp
                180                 185                 190

Val Ile Asn Met Thr Thr Val Pro Glu Val Leu Ala Lys Glu Ala
            195                 200                 205

Gly Ile Cys Tyr Ala Ser Ile Ala Met Ala Thr Asp Tyr Asp Cys Trp
            210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Thr Glu Trp Ser Glu Thr Leu His Asn Leu Lys Met
            260                 265                 270

Ile Lys Phe Gln Met Ile Leu Ser Glu Gly Tyr His Pro Phe Asn Ile
            275                 280                 285

Gln Glu Ser Pro Phe Tyr Arg Gly Leu Leu Asp Phe Pro Ser Val Gly
            290                 295                 300

His Gly Arg Gly Glu Ile Leu Pro Leu Ser Pro Leu Asp Leu Ala Gly
305                 310                 315                 320

Tyr Cys Phe Gln Gln Pro Met Gln Pro Pro Cys Pro Asp Ser
                325                 330

<210> SEQ ID NO 33
<211> LENGTH: 280
<212> TYPE: PRT
<213> ORGANISM: Nomascus leucogenys

<400> SEQUENCE: 33

Met Ala Ser Gly Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
        50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
            100                 105                 110

Phe Ile Asp Arg Thr Thr Met Arg Pro Gln Ser Phe Tyr Asp Gly Ser
            115                 120                 125

His Ser Cys Ala Arg Gly Val Cys His Ile Pro Met Ala Glu Pro Phe
            130                 135                 140
```

```
Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Phe Met Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Thr Glu Trp Ser Glu Thr Leu His Asn Leu Lys Val
                260                 265                 270

Arg Ser Ala Val Gln Leu Pro Pro
                275                 280

<210> SEQ ID NO 34
<211> LENGTH: 283
<212> TYPE: PRT
<213> ORGANISM: Otolemur garnetti

<400> SEQUENCE: 34

Met Ala Leu Ser Ala Ala Ile Ser Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Lys Ile Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Val Ile Ile Asp Gln
                100                 105                 110

Phe Ile Asp Arg Thr Thr Met Arg Pro Gln Thr Phe Tyr Asp Gly Asn
            115                 120                 125

His Ser Cys Thr Arg Gly Val Cys His Ile Pro Met Ala Glu Pro Phe
130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Met Val Thr Ile Glu Gly Pro Arg
                165                 170                 175

Phe Ser Ser Arg Ala Glu Ser Leu Val Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Val Val Ser Val Asp Arg Val Leu Lys Thr Leu
225                 230                 235                 240
```

```
Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asp Leu Lys Asn
            260                 265                 270

Met Ala Gln Phe Ser Val Leu Leu Pro Arg His
            275                 280

<210> SEQ ID NO 35
<211> LENGTH: 283
<212> TYPE: PRT
<213> ORGANISM: Cavia porcellus

<400> SEQUENCE: 35

Met Ala Ser Val Ala Ala Ala Thr Pro Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
            35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Ile Ile Val Thr Thr Ala Cys Gly
            85                  90                  95

Ser Leu Arg Glu Glu Ile Gln Pro Gly Asp Ile Val Ile Ile Asp Gln
            100                 105                 110

Phe Ile Asp Arg Thr Thr Ser Arg Pro Gln Thr Phe Tyr Asp Gly Ser
            115                 120                 125

His Ser Cys Ala Arg Gly Val Cys His Ile Pro Val Ala Glu Pro Phe
        130                 135                 140

Cys Pro Lys Thr Arg Glu Val Leu Ile Glu Thr Ser Lys Lys Leu Gly
145                 150                 155                 160

Leu Arg Cys His Pro Lys Gly Thr Met Ile Thr Ile Glu Gly Pro Arg
                165                 170                 175

Phe Ser Ser Arg Ala Glu Ser Leu Met Phe Arg Thr Trp Gly Ala Asp
            180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Thr Val Ser Val Asp Arg Val Leu Lys Thr Leu
225                 230                 235                 240

Lys Glu Asn Ala Asn Lys Ala Lys Ser Leu Leu Thr Thr Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
            275                 280

<210> SEQ ID NO 36
<211> LENGTH: 285
<212> TYPE: PRT
<213> ORGANISM: Canis lupus

<400> SEQUENCE: 36
```

Met Ala Gln Gly Thr Ser Arg Lys Ser Gln Val Lys Val Ile Gly Ile
1               5                   10                  15

Ile Gly Gly Thr Gly Leu Asp Asp Pro Glu Ile Leu Glu Gly Arg Thr
            20                  25                  30

Glu Lys Tyr Val Asp Thr Pro Phe Gly Lys Pro Ser Asp Ala Leu Ile
        35                  40                  45

Leu Gly Lys Ile Lys Asn Val Asp Cys Val Leu Leu Ala Arg His Gly
    50                  55                  60

Arg Gln His Ser Ile Met Pro Ser Asn Val Asn Tyr Gln Ala Asn Ile
65              70                  75                  80

Trp Ala Leu Lys Glu Glu Gly Cys Thr His Val Ile Val Thr Thr Ala
            85                  90                  95

Cys Gly Ser Leu Arg Glu Glu Ile Gln Pro Gly Asp Ile Val Ile Ile
        100                 105                 110

Asp Gln Phe Ile Asp Arg Thr Thr Lys Arg Pro Gln Thr Phe Tyr Asp
        115                 120                 125

Gly Ser His Ala Cys Ala Arg Gly Val Cys His Ile Pro Met Ala Glu
    130                 135                 140

Pro Phe Cys Pro Lys Thr Arg Glu Val Leu Ile Glu Thr Ala Lys Lys
145                 150                 155                 160

Leu Gly Leu Arg Cys His Ser Lys Gly Ala Met Val Thr Ile Glu Gly
            165                 170                 175

Pro Arg Phe Ser Ser Arg Ala Glu Ser Phe Met Phe Arg Thr Trp Gly
        180                 185                 190

Ala Asp Val Ile Asn Met Thr Thr Val Pro Glu Val Leu Ala Lys
        195                 200                 205

Glu Ala Gly Ile Cys Tyr Ala Ser Ile Ala Met Ala Thr Asp Tyr Asp
    210                 215                 220

Cys Trp Lys Glu His Glu Val Val Ser Val Asp Arg Val Leu Lys
225                 230                 235                 240

Thr Leu Lys Glu Asn Ala Asn Lys Ala Lys Ser Leu Leu Leu Thr Thr
            245                 250                 255

Ile Pro Gln Ile Gly Ser Met Glu Trp Ser Gly Thr Leu His Asn Leu
        260                 265                 270

Lys Asn Met Ala Gln Phe Ser Val Leu Leu Pro Arg His
        275                 280                 285

<210> SEQ ID NO 37
<211> LENGTH: 283
<212> TYPE: PRT
<213> ORGANISM: Mus musculus

<400> SEQUENCE: 37

Met Ala Ser Gly Ser Ala Cys Thr Ala Val Lys Ile Gly Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65              70                  75                  80

Leu Lys Glu Glu Gly Cys Thr His Val Ile Val Thr Thr Ala Cys Gly

```
                        85                  90                  95
Ser Leu Arg Glu Glu Ile Gln Pro Gly Asp Met Val Ile Ile Asp Gln
                100                 105                 110

Phe Ile Asp Arg Thr Ser Leu Arg Pro Gln Thr Phe Tyr Asp Gly Ser
            115                 120                 125

His Cys Ser Ala Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Ile Val Thr Ile Glu Gly Pro Arg
                165                 170                 175

Phe Ser Ser Arg Ala Glu Ser Leu Ile Phe Arg Thr Trp Gly Ala Asp
                180                 185                 190

Val Val Asn Met Thr Thr Val Pro Glu Val Val Leu Ala Lys Glu Ala
                195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Gly Val Leu Lys Thr Met
225                 230                 235                 240

Lys Glu Asn Ala Asn Lys Ala Lys Ser Leu Leu Leu Thr Thr Ile Pro
                245                 250                 255

Gln Ile Gly Ser Met Glu Trp Ser Glu Thr Leu Arg Asn Leu Lys Asn
                260                 265                 270

Met Ala Gln Phe Ser Val Leu Pro Pro Arg His
                275                 280

<210> SEQ ID NO 38
<211> LENGTH: 283
<212> TYPE: PRT
<213> ORGANISM: Pantholops hodgsoni

<400> SEQUENCE: 38

Met Ser Ser Gly Ala Thr Pro Ala Ala Val Lys Ile Gly Ile Ile Gly
1               5                   10                  15

Gly Thr Gly Leu Asp Asp Pro Glu Ile Leu Glu Gly Arg Thr Glu Lys
                20                  25                  30

Tyr Val Asp Thr Pro Phe Gly Lys Pro Ser Asp Ala Leu Val Leu Gly
            35                  40                  45

Lys Ile Lys Asn Val Asp Cys Val Leu Leu Ala Arg His Gly Arg Gln
        50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Lys Glu Glu Ile Gln Pro Gly Asp Ile Ile Ile Asp Gln
                100                 105                 110

Phe Ile Asp Arg Thr Thr Arg Leu Gln Thr Phe Tyr Asp Gly Asn
            115                 120                 125

His Ser Cys Ala Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Val Ile Thr Ile Glu Gly Pro Arg
                165                 170                 175
```

```
Phe Ser Ser Arg Ala Glu Ser Ile Met Phe Gln Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Val Glu Trp Ser Glu Thr Leu His Asn Met Lys Lys
            260                 265                 270

Met Ala Gln Phe Ser Val Leu Leu Pro Arg His
            275                 280

<210> SEQ ID NO 39
<211> LENGTH: 283
<212> TYPE: PRT
<213> ORGANISM: Bos mutus

<400> SEQUENCE: 39

Met Ser Ser Gly Ala Thr Pro Ala Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Val Leu Gly
            35                  40                  45

Lys Ile Lys Asn Val Asp Cys Val Leu Leu Ala Arg His Gly Arg Gln
50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Lys Glu Glu Ile Gln Pro Gly Asp Ile Ile Ile Ile Asp Gln
            100                 105                 110

Phe Ile Asp Arg Thr Thr Arg Arg Leu Gln Thr Phe Tyr Asp Gly Asn
            115                 120                 125

His Ser Cys Ala Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Val Ile Thr Ile Glu Gly Pro Arg
                165                 170                 175

Phe Ser Ser Arg Ala Glu Ser Ile Met Phe Gln Thr Trp Gly Ala Asp
            180                 185                 190

Val Ile Asn Met Thr Thr Val Pro Glu Val Val Leu Ala Lys Glu Ala
        195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Met Glu Trp Ser Glu Thr Leu His Asn Met Lys Lys
            260                 265                 270
```

```
Met Ala Gln Phe Ser Val Leu Leu Pro Arg His
        275                 280

<210> SEQ ID NO 40
<211> LENGTH: 283
<212> TYPE: PRT
<213> ORGANISM: Trichechus manatus

<400> SEQUENCE: 40

Met Ala Ser Gly Ala Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Val Leu Leu Ala Arg His Gly Arg Gln
    50                  55                  60

His Thr Ile Met Pro Ser Lys Val Asn Tyr Gln Ala Asn Ile Trp Ala
65                  70                  75                  80

Leu Lys Glu Glu Gly Cys Thr His Val Ile Val Thr Thr Ala Cys Gly
                85                  90                  95

Ser Leu Arg Glu Glu Ile Gln Pro Gly Asp Ile Ile Ile Asp Gln
            100                 105                 110

Phe Ile Asp Arg Thr Thr Val Arg Pro Gln Thr Phe Tyr Asp Gly Ser
        115                 120                 125

Cys Ser Ser Ala Arg Gly Val Gly His Ile Pro Met Ala Glu Pro Phe
    130                 135                 140

Cys Pro Lys Thr Arg Glu Val Leu Ile Glu Thr Ala Lys Lys Leu Gly
145                 150                 155                 160

Leu Arg Cys His Ser Lys Gly Thr Val Ile Thr Ile Glu Gly Pro Arg
                165                 170                 175

Phe Ser Ser Arg Ala Glu Ser Leu Met Phe Arg Thr Trp Gly Ala Asp
            180                 185                 190

Val Ile Asn Met Thr Thr Val Pro Glu Val Val Leu Ala Lys Glu Ala
        195                 200                 205

Gly Val Cys Tyr Ala Ser Ile Ala Met Ala Thr Asp Tyr Asp Cys Trp
    210                 215                 220

Lys Glu His Glu Glu Ala Val Ser Val Asp Lys Val Leu Lys Thr Leu
225                 230                 235                 240

Lys Glu Asn Ala Asn Lys Ala Lys Ser Leu Leu Leu Thr Thr Ile Pro
                245                 250                 255

Gln Ile Gly Ser Met Glu Trp Ser Glu Thr Leu His Asn Leu Lys Asn
            260                 265                 270

Met Ala Gln Phe Ser Val Leu Leu Pro Arg His
        275                 280

<210> SEQ ID NO 41
<211> LENGTH: 232
<212> TYPE: PRT
<213> ORGANISM: Escherichia coli

<400> SEQUENCE: 41

Met Lys Ile Gly Ile Ile Gly Ala Met Glu Glu Glu Val Thr Leu Leu
1               5                   10                  15

Arg Asp Lys Ile Glu Asn Arg Gln Thr Ile Ser Leu Gly Gly Cys Glu
            20                  25                  30
```

Ile Tyr Thr Gly Gln Leu Asn Gly Thr Glu Val Val Leu Lys Ser
        35                  40                  45

Gly Ile Gly Lys Val Ala Ala Leu Gly Thr Thr Leu Leu Leu Glu
 50                  55                  60

His Cys Lys Pro Asp Val Ile Asn Thr Gly Ser Ala Gly Gly Leu
 65                  70                  75                  80

Ala Pro Thr Leu Lys Val Gly Asp Ile Val Ser Asp Glu Ala Arg
                 85                  90                  95

Tyr His Asp Ala Asp Val Thr Ala Phe Gly Tyr Glu Tyr Gly Gln Leu
                100                 105                 110

Pro Gly Cys Pro Ala Gly Phe Lys Ala Asp Asp Lys Leu Ile Ala Ala
            115                 120                 125

Ala Glu Ala Cys Ile Ala Glu Leu Asn Leu Asn Ala Val Arg Gly Leu
130                 135                 140

Ile Val Ser Gly Asp Ala Phe Ile Asn Gly Ser Val Gly Leu Ala Lys
145                 150                 155                 160

Ile Arg His Asn Phe Pro Gln Ala Ile Ala Val Glu Met Glu Ala Thr
                165                 170                 175

Ala Ile Ala His Val Cys His Asn Phe Asn Val Pro Phe Val Val Val
            180                 185                 190

Arg Ala Ile Ser Asp Val Ala Asp Gln Gln Ser His Leu Ser Phe Asp
        195                 200                 205

Glu Phe Leu Ala Val Ala Ala Lys Gln Ser Ser Leu Met Val Glu Ser
210                 215                 220

Leu Val Gln Lys Leu Ala His Gly
225                 230

<210> SEQ ID NO 42
<211> LENGTH: 231
<212> TYPE: PRT
<213> ORGANISM: Vibrio cholerae

<400> SEQUENCE: 42

Met Lys Ile Gly Ile Ile Gly Ala Met Gln Gln Glu Val Ala Ile Leu
 1               5                  10                  15

Lys Asp Leu Ile Glu Asp Val Gln Glu Val Asn Gln Ala Gly Cys Thr
                20                  25                  30

Phe Tyr Ser Gly Gln Ile Gln Gly Val Asp Val Val Leu Gln Ser
        35                  40                  45

Gly Ile Gly Lys Val Ser Ala Ala Leu Gly Thr Ala Leu Leu Ile Ser
 50                  55                  60

Gln Tyr Ala Pro Asp Val Val Ile Asn Thr Gly Ser Ala Gly Gly Phe
 65                  70                  75                  80

Asp Ala Ser Leu Asn Val Gly Asp Val Ile Ser Ser Glu Val Arg
                 85                  90                  95

His His Asp Ala Asp Val Thr Ala Phe Gly Tyr Glu Ile Gly Gln Met
                100                 105                 110

Ala Gly Gln Pro Ala Ala Phe Lys Ala Asp Asp Lys Leu Met Thr Val
            115                 120                 125

Ala Glu Gln Ala Leu Ala Gln Leu Pro Asn Thr His Ala Val Arg Gly
130                 135                 140

Leu Ile Cys Thr Gly Asp Ala Phe Val Cys Thr Ala Glu Arg Gln Gln
145                 150                 155                 160

Phe Ile Arg Gln His Phe Pro Ser Val Val Ala Val Glu Met Glu Ala 165                 170                 175
Ser Ala Ile Ala Gln Thr Cys His Gln Phe Lys Val Pro Phe Val Val
            180                 185                 190

Val Arg Ala Ile Ser Asp Val Ala Asp Lys Glu Ser Pro Leu Ser Phe
            195                 200                 205

Glu Glu Phe Leu Pro Leu Ala Ala Lys Ser Ser Ala Met Val Leu
            210                 215                 220

Lys Met Val Glu Leu Leu Lys
225                 230

<210> SEQ ID NO 43
<211> LENGTH: 231
<212> TYPE: PRT
<213> ORGANISM: Helicobacter pylori

<400> SEQUENCE: 43

Met Val Gln Lys Ile Gly Ile Leu Gly Ala Met Arg Glu Glu Ile Thr
1               5                   10                  15

Pro Ile Leu Glu Leu Phe Gly Val Asp Phe Glu Ile Ser Leu Gly
            20                  25                  30

Gly Asn Val Phe His Lys Gly Val Tyr Asn Gly Lys Glu Ile Val Val
            35                  40                  45

Ala Tyr Ser Lys Ile Gly Lys Val His Ser Thr Leu Thr Thr Thr Ser
50                  55                  60

Met Ile Leu Ala Phe Gly Val Gln Lys Val Leu Phe Ser Gly Val Ala
65                  70                  75                  80

Gly Ser Leu Ile Lys Asp Leu Lys Ile Asn Asp Leu Leu Val Ala Ile
            85                  90                  95

Gln Leu Val Gln His Asp Val Asp Leu Ser Ala Phe Asn His Pro Leu
            100                 105                 110

Gly Phe Ile Pro Glu Ser Ala Ile Phe Ile Glu Thr Ser Glu Ser Leu
            115                 120                 125

Asn Ala Leu Ala Lys Lys Val Ala Asn Glu Gln His Ile Ala Leu Lys
130                 135                 140

Glu Gly Val Ile Ala Ser Gly Asp Gln Phe Val His Ser Lys Glu Arg
145                 150                 155                 160

Lys Glu Phe Leu Val Ser Glu Phe Lys Ala Ser Ala Val Glu Met Glu
            165                 170                 175

Gly Ala Ser Val Ala Phe Val Cys Gln Lys Phe Gly Val Pro Cys Cys
            180                 185                 190

Val Leu Arg Ser Ile Ser Asp Asn Ala Asp Glu Ala Asn Met Ser
            195                 200                 205

Phe Asp Ala Phe Leu Glu Lys Ser Ala Gln Thr Ser Ala Lys Phe Leu
210                 215                 220

Lys Ser Met Val Asp Lys Leu
225                 230

<210> SEQ ID NO 44
<211> LENGTH: 228
<212> TYPE: PRT
<213> ORGANISM: Staphylococcus aureus

<400> SEQUENCE: 44

Met Ile Gly Ile Ile Gly Ala Met Glu Glu Glu Val Thr Ile Leu Lys
1               5                   10                  15

Asn Lys Leu Thr Gln Leu Ser Glu Ile Ser Val Ala His Val Lys Phe

```
                    20                  25                  30
Tyr Thr Gly Ile Leu Lys Asp Arg Glu Val Val Ile Thr Gln Ser Gly
             35                  40                  45
Ile Gly Lys Val Asn Ala Ala Ile Ser Thr Thr Leu Leu Ile Asn Lys
 50                  55                  60
Phe Lys Pro Asp Val Ile Ile Asn Thr Gly Ser Ala Gly Ala Leu Asp
 65                  70                  75                  80
Glu Ser Leu Asn Val Gly Asp Val Leu Ile Ser Asp Val Lys Tyr
                 85                  90                  95
His Asp Ala Asp Ala Thr Ala Phe Gly Tyr Glu Tyr Gly Gln Ile Pro
                100                 105                 110
Gln Met Pro Val Ala Phe Gln Ser Ser Lys Pro Leu Ile Glu Lys Val
                115                 120                 125
Ser Gln Val Val Lys Gln Gln Leu Thr Ala Lys Val Gly Leu Ile
                130                 135                 140
Val Ser Gly Asp Ser Phe Ile Gly Ser Val Glu Gln Arg Gln Lys Ile
145                 150                 155                 160
Lys Lys Ala Phe Pro Asn Ala Met Ala Val Glu Met Glu Ala Thr Ala
                165                 170                 175
Ile Ala Gln Thr Cys Tyr Gln Phe Asn Val Pro Phe Val Val Val Arg
                180                 185                 190
Ala Val Ser Asp Leu Ala Asn Gly Glu Ala Glu Met Ser Phe Glu Ala
                195                 200                 205
Phe Leu Glu Lys Ala Ala Val Ser Ser Ser Gln Thr Val Glu Ala Leu
                210                 215                 220
Val Ser Gln Leu
225

<210> SEQ ID NO 45
<211> LENGTH: 237
<212> TYPE: PRT
<213> ORGANISM: Borrelia burgdorferi

<400> SEQUENCE: 45

Met Ile Leu Ile Ile Ser Ala Met Gln Glu Ser Glu Glu Ile Asn
  1               5                  10                  15
Lys Met Leu Asp Asn Lys Glu Glu Ile Val Leu Asn Asp Tyr Leu Glu
                 20                  25                  30
Asn Lys Lys Ile Tyr Lys Gly Lys Ile Leu Gly Lys Asp Val Ile Ser
             35                  40                  45
Leu Thr Thr Gly Ile Gly Lys Val Asn Ala Ala Thr Trp Ser Ser Gln
 50                  55                  60
Ile Ile Ser Lys Tyr Lys Ile Thr His Ile Ile Asn Ser Gly Ser Ser
 65                  70                  75                  80
Gly Gly Ile Lys Glu Asn Ser Asn Leu Lys Ile Leu Asp Ile Ile Val
                 85                  90                  95
Ser Ser Glu Thr Ala Tyr Tyr Asp Phe Asp Leu Thr Lys Phe Gly His
                100                 105                 110
Lys Ile Gly Gln Val Pro Asn Leu Pro Gln Lys Phe Lys Ala Asp Glu
                115                 120                 125
Glu Leu Leu Lys Lys Val Ala Asn Ile Val Asp Asn Lys Leu Leu Asn
                130                 135                 140
Ile Asp Ile His Ile Gly Leu Ile Leu Thr Gly Asp Gln Phe Val Asp
145                 150                 155                 160
```

```
Asn Glu Lys Asn Leu Glu Thr Ile Lys Lys Asn Phe Lys Asp Ala Leu
            165                 170                 175

Ala Val Asp Met Glu Gly Ala Ala Ile Ala Gln Val Ala His Ile Phe
        180                 185                 190

Lys Ile Pro Phe Ile Ile Ile Arg Ser Ile Ser Asp Leu Pro Asn Asn
            195                 200                 205

Lys Asp Asn His Ile Asp Phe Asn Lys Phe Leu Lys Thr Ser Ser Ile
        210                 215                 220

Asn Ser Ser Lys Met Thr Lys Glu Leu Ile Arg Leu Ile
225                 230                 235

<210> SEQ ID NO 46
<211> LENGTH: 229
<212> TYPE: PRT
<213> ORGANISM: Streptococcus pneumoniae

<400> SEQUENCE: 46

Met Lys Ile Gly Ile Val Gly Ala Met Ala Gln Glu Val Glu Ile Leu
1               5                   10                  15

Lys Asn Leu Met Ala Asp Arg Thr Glu Thr Cys Val Ala Ser Ala Val
            20                  25                  30

Ile Phe Glu Gly Lys Ile Asn Gly Lys Asn Val Ala Leu Leu Gln Ser
        35                  40                  45

Gly Ile Gly Lys Val Ala Ala Ile Gly Thr Thr Ala Leu Leu Gln
    50                  55                  60

Leu Ala Lys Pro Asp Phe Val Ile Asn Thr Gly Ser Ala Gly Val
65                  70                  75                  80

Ala Lys Gly Leu Lys Val Gly Asp Ile Val Ile Ser Asp Glu Thr Arg
            85                  90                  95

Tyr His Asp Ala Asp Val Thr Ala Phe Gly Tyr Glu Lys Gly Gln Leu
        100                 105                 110

Pro Ala Asn Pro Ala Ala Phe Leu Ser Asp Lys Lys Leu Ala Asp Leu
    115                 120                 125

Ala Gln Glu Ile Ala Glu Lys Gln Gly Gln Ser Val Lys Arg Gly Leu
130                 135                 140

Ile Cys Ser Gly Asp Ser Phe Ile Asn Ser Glu Asp Lys Ile Thr Gln
145                 150                 155                 160

Ile Lys Ala Asp Phe Pro Asn Val Met Gly Val Glu Met Glu Ala Thr
            165                 170                 175

Ala Ile Ala Gln Val Cys Tyr Ala Phe Asn Val Pro Phe Val Val Val
        180                 185                 190

Arg Ala Ile Ser Asp Gly Gly Asp Gly Lys Ala Ser Ile Ser Phe Glu
    195                 200                 205

Glu Phe Leu Pro Leu Ala Ala Lys Gln Ser Ser Ala Leu Val Leu Gly
    210                 215                 220

Met Ile Asp Arg Leu
225

<210> SEQ ID NO 47
<211> LENGTH: 233
<212> TYPE: PRT
<213> ORGANISM: Neisseria meningitidis

<400> SEQUENCE: 47

Met Ser Leu Lys Thr Val Ala Val Ile Gly Ala Met Glu Gln Glu Ile
1               5                   10                  15
```

```
Glu Leu Leu Arg Glu Met Met Glu Asn Val Lys Ala Val Ser Phe Gly
             20                  25                  30

Lys Phe Thr Ala Tyr Glu Gly Glu Leu Ala Gly Lys Arg Met Val Leu
         35                  40                  45

Ala Leu Ser Gly Ile Gly Lys Val Asn Ala Ala Val Ala Thr Ala Trp
 50                  55                  60

Ile Ile Arg Glu Phe Ala Ala Asp Cys Val Ile Asn Thr Gly Ser Ala
 65                  70                  75                  80

Gly Gly Leu Gly Lys Gly Leu Lys Val Ser Asp Val Val Ile Gly Thr
                 85                  90                  95

Glu Thr Ala His His Asp Val Asp Val Thr Ala Phe Gly Tyr Val Trp
            100                 105                 110

Gly Gln Val Pro Gln Leu Pro Ala Val Phe Val Ser Asp Asp Leu Leu
            115                 120                 125

Val Gly Lys Ala Lys Arg Ala Ala Arg Thr Phe Glu Gly Ala Ala Val
130                 135                 140

Glu Gln Gly Leu Ile Val Ser Gly Asp Arg Phe Val His Ser Ser Glu
145                 150                 155                 160

Gly Val Ala Glu Ile Arg Lys His Phe Pro Glu Val Lys Ala Val Glu
                165                 170                 175

Met Glu Ala Ala Ala Ile Ala Gln Thr Cys His Gln Leu Glu Thr Pro
            180                 185                 190

Phe Val Ile Ile Arg Ala Val Ser Asp Ser Ala Asp Glu Lys Ala Asp
            195                 200                 205

Ile Ser Phe Asp Glu Phe Leu Lys Thr Ala Ala Val Ser Ser Ala Lys
            210                 215                 220

Met Val Thr Glu Ile Val Lys Ser Leu
225                 230

<210> SEQ ID NO 48
<211> LENGTH: 231
<212> TYPE: PRT
<213> ORGANISM: Weissella paramesenteroides

<400> SEQUENCE: 48

Met Arg Tyr Gly Val Ile Asn Ala Met Ala Glu Glu Lys Ala Ala Leu
 1               5                  10                  15

Val Asp Ala Met Ile Asp Glu Lys Lys Thr Thr Ile Ala Gly Lys Leu
             20                  25                  30

Phe His His Gly Lys Ile Gly His Val Asp Val Val Val Glu Ser
         35                  40                  45

Gly Ile Gly Lys Val Ala Ser Ala Leu Thr Thr Thr Leu Leu Ile Thr
 50                  55                  60

Asn Phe Gly Val Asp Ala Val Ile Asn Ser Ser Ala Gly Ala Leu
 65                  70                  75                  80

Gly Thr Asp Leu Arg Ile Gly Asp Ile Val Ile Ala Asp Tyr Leu Ala
                 85                  90                  95

Tyr Ala Asp Ala Asp Ala Arg Ala Phe Gly Tyr Ala Tyr Gly Gln Val
            100                 105                 110

Pro Gln Gln Pro Ala Arg Phe Lys Ala Asp Thr Asp Leu Ser Asn Asp
            115                 120                 125

Leu Ser Glu Ser Tyr Glu Lys Val Thr Asp Ala Arg Leu Val Arg Gly
        130                 135                 140

Leu Val Val Thr Ser Asp Ser Phe Ile Ala Ser Asn Glu Gln Lys Gln
145                 150                 155                 160
```

```
Thr Ile Leu Thr His Phe Pro Glu Ala Gln Ser Ala Glu Met Glu Gly
            165                 170                 175

Ala Ser Ile Ala Gln Val Ala Asn Tyr Phe Asp Val Pro Phe Ala Val
            180                 185                 190

Val Arg Ala Ile Ser Asp Asn Ala Asn Gly Glu Ala Gly Met Thr Phe
            195                 200                 205

Asp Asp Phe Ile Val Glu Ala Gly Gln Gln Ser Ala Gln Val Leu Ile
            210                 215                 220

Asn Phe Phe Glu Ala Gln Ala
225                 230

<210> SEQ ID NO 49
<211> LENGTH: 237
<212> TYPE: PRT
<213> ORGANISM: Sulfurimonas denitrificans

<400> SEQUENCE: 49

Met Lys Ile Ala Ile Met Gly Ala Met Pro Glu Glu Ile Ser Pro Ile
1               5                   10                  15

Leu Glu Lys Ile Gly Ser Tyr Lys Ser Thr Ser Tyr Ala Gly Asn Lys
            20                  25                  30

Tyr Tyr Glu Ala Thr Tyr Gln Gly Val Glu Leu Val Ile Ala Tyr Ser
        35                  40                  45

Lys Ile Gly Lys Val Phe Ser Ala Leu Ser Ala Ala Thr Met Ile Glu
50                  55                  60

His Phe Gly Ala Thr Lys Leu Leu Phe Ser Gly Val Ala Gly Ala Ile
65                  70                  75                  80

Ser Thr Asn Leu Lys Val Gly Asp Leu Ile Val Ala Thr Lys Leu Ser
            85                  90                  95

Gln His Asp Leu Asp Ile Thr Ala Phe Gly His Pro Tyr Gly Tyr Val
            100                 105                 110

Pro Glu Gly Ser Val Phe Val Glu Ala Asp Lys Asp Met Ile Glu Leu
            115                 120                 125

Ser Lys Lys Val Ala Leu Glu Met Gly Lys Ser Val Gln Glu Gly Ile
130                 135                 140

Ile Ala Thr Gly Asp Gln Phe Val Ala Asn Glu Glu Arg Lys Asn Trp
145                 150                 155                 160

Ile Gly Thr Thr Phe Gly Ala Asp Ala Leu Glu Met Glu Gly Gly Ser
            165                 170                 175

Val Gly Val Val Cys Asn Ala Leu Asn Ile Pro Phe Phe Ile Leu Arg
            180                 185                 190

Ser Ile Ser Asp Ala Ala Asp Met Asp Ala Ser Phe Ser Phe Asp Glu
            195                 200                 205

Phe Leu Glu Ser Ser Ala Lys Glu Ser Ala Glu Phe Ile Met Lys Met
            210                 215                 220

Val Asp Glu Leu Val Ala Leu Pro Leu Gln Asp Ile Lys
225                 230                 235

<210> SEQ ID NO 50
<211> LENGTH: 230
<212> TYPE: PRT
<213> ORGANISM: Aeromonas hydrophila

<400> SEQUENCE: 50

Met Lys Val Gly Ile Ile Gly Ala Met Glu Gln Glu Val Ala Leu Leu
1               5                   10                  15
```

```
Arg Ser Gln Met Ser Asn Pro Thr Thr Leu Gln Leu Gly Gly Cys Glu
            20              25              30
Phe Tyr Gln Gly Ser Leu Ala Gly Lys Glu Val Ile Leu Thr Arg Ser
            35              40              45
Gly Ile Gly Lys Val Ala Ala Ser Val Ala Thr Ser Leu Leu Leu Glu
 50              55              60
Lys Phe Ala Pro Asp Tyr Val Ile Asn Thr Gly Ser Ala Gly Gly Phe
 65              70              75              80
Ala Gln Asp Leu His Ile Gly Asp Val Val Ile Ala Ser Glu Met Arg
            85              90              95
Phe His Asp Val Asp Val Thr Ala Phe Gly Tyr Glu Met Gly Gln Met
            100             105             110
Ala Gln Gln Pro Ala Ala Phe Pro Cys Asp Glu Lys Leu Ile Ala Val
            115             120             125
Ala Gln Asp Cys Ile Ala Glu Gln Gly Lys His Gln Thr Lys Val Gly
 130             135             140
Leu Ile Cys Thr Gly Asp Gln Phe Met Cys Lys Pro Asp Ala Ile Ala
145             150             155             160
Lys Ala Arg Ala Asp Phe Pro Gln Met Leu Ala Val Glu Met Glu Gly
            165             170             175
Ala Ala Ile Gly Gln Val Cys His Met Phe Lys Val Pro Tyr Leu Val
            180             185             190
Val Arg Ala Met Ser Asp Ile Ala Gly Lys Glu Gln Val Glu Ser Phe
            195             200             205
Asp Ala Phe Ile Glu Val Ala Gly Lys His Ser Ala Glu Val Ile Ile
            210             215             220
Lys Met Leu Gly Lys Leu
225             230
```